US012649719B2

(12) United States Patent
Li

(10) Patent No.: US 12,649,719 B2
(45) Date of Patent: Jun. 9, 2026

(54) MODULATORS OF HEMOGLOBIN

(71) Applicant: Global Blood Therapeutics, Inc., South San Francisco, CA (US)

(72) Inventor: Zhe Li, San Diego (CA)

(73) Assignee: Global Blood Therapeutics, Inc., South San Francisco, CA (US)

( * ) Notice: Subject to any disclaimer, the term of this patent is extended or adjusted under 35 U.S.C. 154(b) by 926 days.

(21) Appl. No.: 17/914,932

(22) PCT Filed: Mar. 26, 2021

(86) PCT No.: PCT/US2021/024384
§ 371 (c)(1),
(2) Date: Sep. 27, 2022

(87) PCT Pub. No.: WO2021/202284
PCT Pub. Date: Oct. 7, 2021

(65) Prior Publication Data

US 2023/0192611 A1 Jun. 22, 2023

Related U.S. Application Data

(60) Provisional application No. 63/003,104, filed on Mar. 31, 2020, provisional application No. 63/003,106, filed on Mar. 31, 2020.

(51) Int. Cl.

| | |
|---|---|
| ***C07D 211/22*** | (2006.01) |
| ***A61P 7/06*** | (2006.01) |
| ***C07D 265/30*** | (2006.01) |
| ***C07D 279/12*** | (2006.01) |
| ***C07D 401/06*** | (2006.01) |
| ***C07D 413/06*** | (2006.01) |
| ***C07D 417/06*** | (2006.01) |

(52) U.S. Cl.
CPC .............. *C07D 211/22* (2013.01); *A61P 7/06* (2018.01); *C07D 265/30* (2013.01); *C07D 279/12* (2013.01); *C07D 401/06* (2013.01); *C07D 413/06* (2013.01); *C07D 417/06* (2013.01); *C07B 2200/07* (2013.01)

(58) Field of Classification Search
CPC .................................................... C07D 211/22
See application file for complete search history.

(56) References Cited

U.S. PATENT DOCUMENTS

| | | | | |
|---|---|---|---|---|
| 10,683,285 | B2 * | 6/2020 | Li | C07D 207/08 |
| 11,014,884 | B2 * | 5/2021 | Metcalf | C07D 405/12 |
| 11,548,880 | B2 * | 1/2023 | Li | C07D 401/10 |

FOREIGN PATENT DOCUMENTS

| | | |
|---|---|---|
| WO | WO 2016/043849 | 3/2016 |

OTHER PUBLICATIONS

International Search Report and Written Opinion dated May 14, 2021 for PCT Application No. PCT/US2021/024384. 14 pages.

* cited by examiner

*Primary Examiner* — Golam M Shameem

(57) ABSTRACT

The present disclosure relates generally to compounds and pharmaceutical compositions suitable as modulators of hemoglobin and methods for their use in treating disorders mediated by hemoglobin. (Formula (I))

I

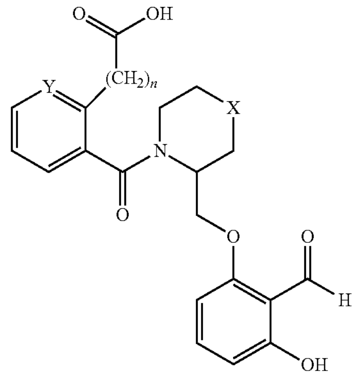

20 Claims, No Drawings

MODULATORS OF HEMOGLOBIN

CROSS-REFERENCE TO RELATED APPLICATIONS

This application is a U.S. National Stage Application under 35 U.S.C. § 371 of International Application No. PCT/US2021/024384, filed Mar. 26, 2021, which claims the benefit under 35 U.S.C. § 119(e) of U.S. Provisional Application No. 63/003,106, filed Mar. 31, 2020, and U.S. Provisional Application No. 63/003,104, filed Mar. 31, 2020, each of which is hereby incorporated by reference in its entirety.

FIELD

Provided herein are compounds and pharmaceutical compositions suitable as modulators of hemoglobin, and methods for their use in treating disorders mediated by hemoglobin.

BACKGROUND

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin A (HbA).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels.

2-hydroxy-6-((2-(1-isopropyl-1H-pyrazol-5-yl)pyridin-3-yl)methoxy)benzaldehyde (also known as voxelotor or GBT440), a modulator of hemoglobin that increases the affinity of hemoglobin for oxygen and consequently inhibits polymerization of HbS when subjected to hypoxic conditions, is approved by the U.S. Food and Drug Administration (FDA) for the treatment of sickle cell disease.

WO 2014/150268 describes modulators of hemoglobin that are structurally related to the compounds disclosed herein.

A need exists for compounds having a suitable pharmacokinetic profile and efficacy in the treatment of disorders mediated by abnormal Hb such as HbS and for methods of treating such disorders.

SUMMARY

Provided herein is a compound of formula I:

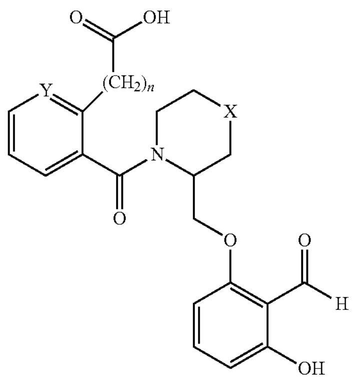

I or an isotopically enriched analog, stereoisomer, mixture of stereoisomers, or prodrug thereof, or a pharmaceutically acceptable salt of each thereof, wherein:

Y is CH or N;

X is $CH_2$, O, or S; and n is 0, 1, or 2.

Also provided herein is a compound of formula II:

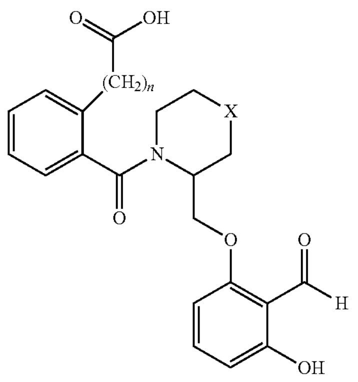

II or an isotopically enriched analog, stereoisomer, mixture of stereoisomers, or prodrug thereof, or a pharmaceutically acceptable salt of each thereof, wherein:

X is $CH_2$, O, or S; and n is 0, 1, or 2.

Also provided herein is a compound of formula III:

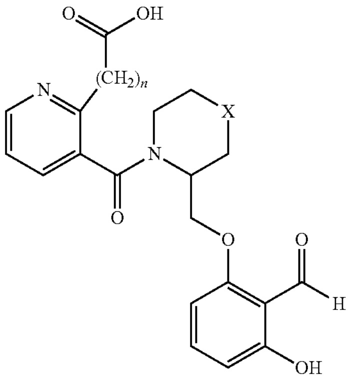

III or an isotopically enriched analog, stereoisomer, mixture of stereoisomers, or prodrug thereof, or a pharmaceutically acceptable salt of each thereof, wherein:

X is $CH_2$, O, or S; and n is 0, 1, or 2.

Also provided herein are pharmaceutical compositions comprising a compound as described herein, or an isotopically enriched analog, stereoisomer, mixture of stereoisomers, or prodrug thereof, or a pharmaceutically acceptable salt of each thereof, and a pharmaceutically acceptable excipient. Some embodiments provide for pharmaceutical compositions comprising a compound as described herein or a pharmaceutically acceptable salt thereof, and a pharmaceutically acceptable excipient. Some embodiments provide for pharmaceutical compositions comprising a compound as described herein and a pharmaceutically acceptable excipient.

Also provided herein are methods for modulating (e.g., increasing) oxygen affinity of hemoglobin (e.g., hemoglobin S) in a subject in need thereof, comprising administering to the subject a compound as described herein, or an isotopically enriched analog, stereoisomer, mixture of stereoisomers, or prodrug thereof, or a pharmaceutically acceptable salt of each thereof, or a pharmaceutical composition as described herein.

Also provided herein are methods for treating a disorder mediated by hemoglobin in a subject in need thereof, comprising administering to the subject a compound as described herein, or an isotopically enriched analog, stereoisomer, mixture of stereoisomers, or prodrug thereof, or a pharmaceutically acceptable salt of each thereof, or a pharmaceutical composition as described herein.

Also provided herein are methods for treating sickle cell disease in a subject in need thereof, comprising administering to the subject a compound as described herein, or an isotopically enriched analog, stereoisomer, mixture of stereoisomers, or prodrug thereof, or a pharmaceutically acceptable salt of each thereof, or a pharmaceutical composition as described herein.

DETAILED DESCRIPTION

Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms. In another example, "$C_{1-4}$ alkyl" indicates that the alkyl group has from 1 to 4 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last-mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O-". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-$S(O)_2$—".

"Acyl" refers to a group —C(O)$R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)N$R^yR^z$ and an "N-amido" group which refers to the group —N$R^y$C(O)$R^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group —N$R^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(N$R^y$)(N$R^z_2$), wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Arylalkyl" or "Aralkyl" refers to the group "aryl-alkyl-".

"Carbamoyl" refers to both an "O-carbamoyl" group which refers to the group —O—C(O)N$R^yR^z$ and an "N-carbamoyl" group which refers to the group —N$R^y$C(O)O$R^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)$R^x$ and —C(O)O$R^x$, wherein $R^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to —N$R^y$C(=N$R^z$)(N$R^yR^z$), wherein each $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Imino" refers to a group —C(N$R^y$)$R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)N$R^y$C(O)$R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6, or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, or 1 to 3) hydrogen atoms are replaced by a halogen.

"Hydroxyalkyl" refers to an alkyl group as defined above, wherein one or more (e.g., 1 to 6, or 1 to 3) hydrogen atoms are replaced by a hydroxy group. A "mono-hydroxy-($C_{1-4}$ alkyl)" refers to a $C_{1-4}$ alkyl group as defined above, wherein one hydrogen atom is replaced by a hydroxy group. A "di-hydroxy-($C_{1-4}$ alkyl)" refers to a $C_{1-4}$ alkyl group as defined above, wherein two hydrogen atoms are replaced by hydroxy groups.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —$NR^y$—, —O—, —S—, —S(O)—, —$S(O)_2$—, and the like, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl.

Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group —$CR^y$(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups $—SO_2NR^yR^z$ and $—NR^ySO_2R^z$, where $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, $—NHNH_2$, $=NNH_2$, imino, imido, hydroxy, oxo, oxime, nitro, sulfonyl, sulfinyl, alkylsulfonyl, alkylsulfinyl, thiocyanate, —S(O)OH, $—S(O)_2OH$, sulfonamido, thiol, thioxo, N-oxide or $—Si(R^y)_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, $—NR^gR^h$, $—NR^gC(=O)Rh$, $—NR^gC(=O)NR^gR^h$, $—NR^gC(=O)OR^h$, $—NR^gS(=O)_{1-2}R^h$, $—C(=O)R^g$, $—C(=O)OR^g$, $—OC(=O)OR^g$, $—OC(=O)R^g$, $—C(=O)NR^gR^h$, $—OC(=O)NR^gR^h$, $—OR^g$, $—SR^g$, $—S(=O)R^g$, $—S(=O)_2R^g$, $—OS(=O)_{1-2}R^g$, $—S(=O)_{1-2}OR^g$, $—NR^gS(=O)_{1-2}NR^gR^h$, $=NSO_2R^g$, $=NOR^g$, $—S(=O)_{1-2}NR^gR^h$, $—SF_5$, $—SCF_3$ or $—OCF_3$. In certain embodiments, "substituted" also means any of the above groups in which one or more (e.g., 1 to 5, or 1 to 3) hydrogen atoms are replaced with $—C(=O)R^g$, $—C(=O)OR^g$, $—C(=O)NR^gR^h$, $—CH_2SO_2R^g$, or $—CH_2SO_2NR^gR^h$. In the foregoing, R and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like. In some embodiments, a pharmaceutically acceptable salt does not include a salt of a primary amine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound.

Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the disclosure may be reduced in vivo to a —$CH_2OH$ moiety.

The term "hydroxy protecting group" refers to a chemical moiety which is added to, and later removed from, a hydroxy functionality to obtain chemoselectivity in a subsequent chemical reaction. Exemplary protecting groups, as well as the methods for deprotection, include, but are not limited to, acetyl (Ac) (removed by acid or base), benzoyl (Bz) (removed by acid or base), benzyl (Bn) (removed by hydrogenolysis), β-methoxyethoxymethyl ether (MEM) (removed by acid), dimethoxytrityl or [bis-(4-methoxyphenyl)phenylmethyl](DMT) (removed by weak acid), methoxymethyl ether (MOM) (removed by acid), methoxytrityl or [(4-methoxyphenyl)diphenylmethyl](MMT) (removed by acid and hydrogenolysis), p-methoxybenzyl ether (PMB) (removed by acid, hydrogenolysis, or oxidation), methylthiomethyl ether (removed by acid), pivaloyl (Piv) (removed by acid, base or reductant agents), tetrahydropyranyl (THP) (removed by acid), tetrahydrofuran (THF) (removed by acid), trityl (triphenylmethyl, Tr) (removed by acid and hydrogenolysis), silyl ether (e.g., trimethylsilyl (TMS), tert-butyldimethylsilyl (TBDMS), tri-iso-propylsilyloxymethyl (TOM), and triisopropylsilyl (TIPS) ethers) (removed by acid or fluoride ion, such as NaF, TBAF (tetra-n-butylammonium fluoride, HF-Py, or HF-NEt3)), methyl ethers (removed by cleavage is by TMSI in dichloromethane or acetonitrile or chloroform, or BBr3 in DCM), ethoxyethyl ethers (EE) (removed by 1N hydrochloric acid).

Compounds

Provided herein are compounds that are useful as modulators of hemoglobin. It is contemplated that certain compounds disclosed herein have an improved pharmacokinetic profile.

Provided herein is a compound of formula I:

I

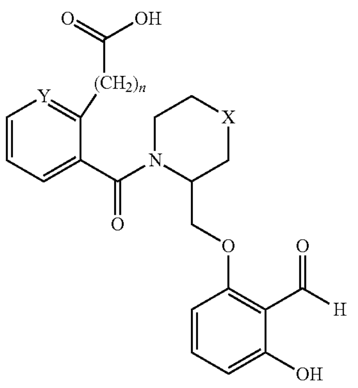

or an isotopically enriched analog, stereoisomer, mixture of stereoisomers, or prodrug thereof, or a pharmaceutically acceptable salt of each thereof, wherein Y, X, and n are as defined herein.

Provided herein is a compound of formula II:

II

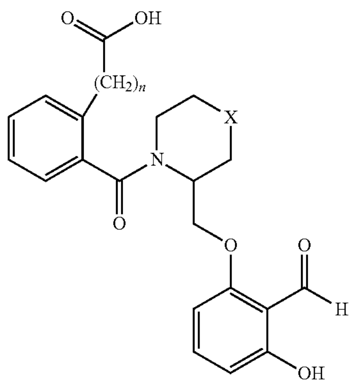

or an isotopically enriched analog, stereoisomer, mixture of stereoisomers, or prodrug thereof, or a pharmaceutically acceptable salt of each thereof, wherein X and n are as defined herein.

Provided herein is a compound of formula 11(a):

II(a)

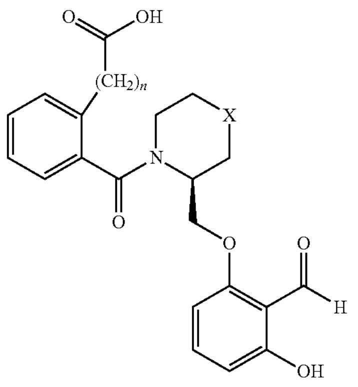

or an isotopically enriched analog or prodrug thereof, or a pharmaceutically acceptable salt of each thereof, wherein X and n are as defined herein.

Provided herein is a compound of formula 11(b):

II(b)

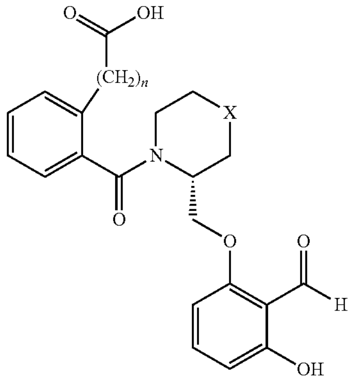

or an isotopically enriched analog or prodrug thereof, or a pharmaceutically acceptable salt of each thereof, wherein X and n are as defined herein.

Provided herein is a compound of formula III:

III

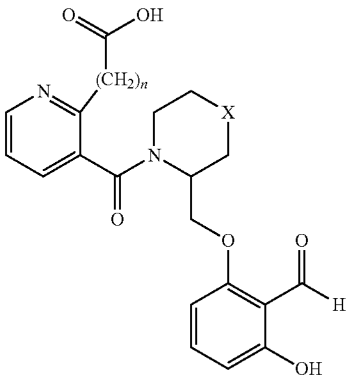

or an isotopically enriched analog, stereoisomer, mixture of stereoisomers, or prodrug thereof, or a pharmaceutically acceptable salt of each thereof, wherein X and n are as defined herein.

Provided herein is a compound of formula 111(a):

III(a)

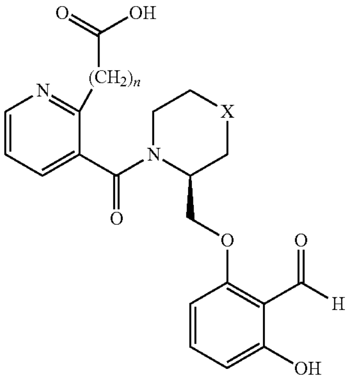

or an isotopically enriched analog or prodrug thereof, or a pharmaceutically acceptable salt of each thereof, wherein X and n are as defined herein.

Provided herein is a compound of formula III(b):

III(b)

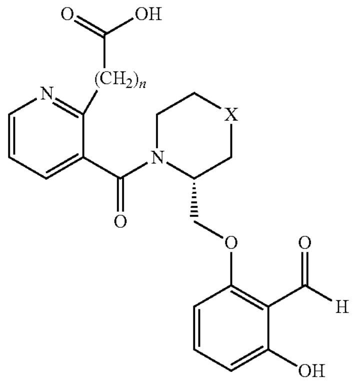

or an isotopically enriched analog or prodrug thereof, or a pharmaceutically acceptable salt of each thereof, wherein X and n are as defined herein.

In some embodiments, Y is CH or N. In some embodiments, Y is CH. In some embodiments, Y is N.

In some embodiments, X is $CH_2$, O, or S. In some embodiments, X is $CH_2$. In some embodiments, X is O. In some embodiments, X is S.

In some embodiments, n is 0, 1, or 2. In some embodiments, n is 0. In some embodiments, n is 1 or 2. In some embodiments, n is 1. In some embodiments, n is 2.

Any of the combinations of Y, X, and n are encompassed and provided by this disclosure.

Provided herein is a compound selected from Table 1, or an isotopically enriched analog, stereoisomer, mixture of stereoisomers, or prodrug thereof, or a pharmaceutically acceptable salt of each thereof. Provided herein is a compound selected from Table 1, or a pharmaceutically acceptable salt thereof. Provided herein is a compound selected from Table 1.

Provided herein is a compound selected from Table 2, or an isotopically enriched analog or prodrug thereof, or a pharmaceutically acceptable salt of each thereof. Provided herein is a compound selected from Table 2, or a pharmaceutically acceptable salt thereof.

Provided herein is a compound selected from Table 2.

Compound numbers and IUPAC names of compounds described herein are summarized in Table 1.

TABLE 1
| Compound Number | Structure | IUPAC name |
|---|---|---|
| 1A | 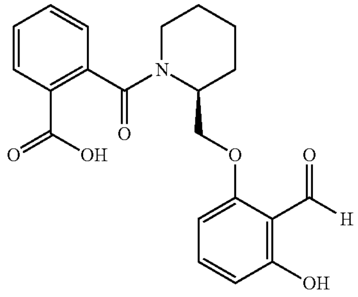 [SMILES: O=Cc1c(O)cccc1OC[C@@H]1CCCCN1C(=O)c1ccccc1C(=O)O] | 2-[(2S)-2-[(2-formyl-3-hydroxyphenoxy)methyl]piperidine-1-carbonyl]benzoic acid |
| 2A | 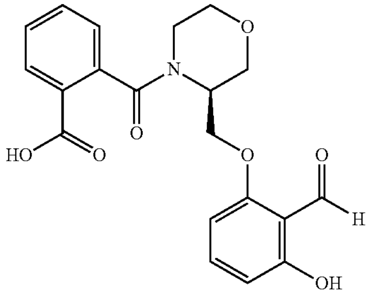 | 2-[(3S)-3-[(2-formyl-3-hydroxyphenoxy)methyl]morpholine-4-carbonyl]benzoic acid |
| 3A | 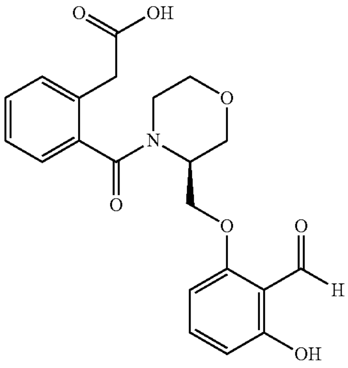 [SMILES: O=Cc1c(O)cccc1OC[C@@H]1COCCN1C(=O)c1ccccc1CC(=O)O] | 2-{2-[(3S)-3-[(2-formyl-3-hydroxyphenoxy)methyl]morpholine-4-carbonyl]phenyl}acetic acid |
| 4A | 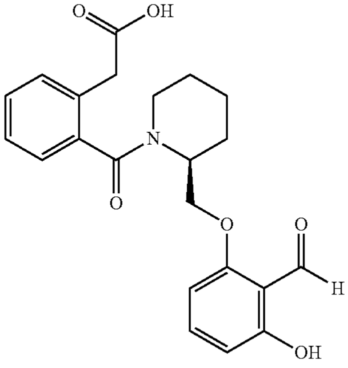 [SMILES: O=Cc1c(O)cccc1OC[C@@H]1CCCCN1C(=O)c1ccccc1CC(=O)O] | 2-{2-[(2S)-2-[(2-formyl-3-hydroxyphenoxy)methyl]piperidine-1-carbonyl]phenyl} acetic acid |

TABLE 1-continued

| Compound Number | Structure | IUPAC name |
| --- | --- | --- |
| 5A (Enantiomer 1) | 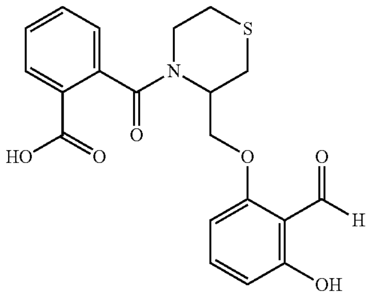 [SMILES: O=Cc1c(O)cccc1OCC1CSCCN1C(=O)c1ccccc1C(=O)O] | 2-(3-((2-formyl-3-hydroxyphenoxy)methyl) thiomorpholine-4-carbonyl) benzoic acid |
| 5A (Enantiomer 2) | 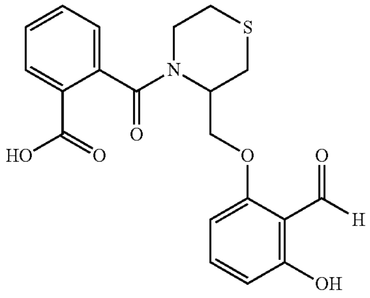 | 2-(3-((2-formyl-3-hydroxyphenoxy)methyl) thiomorpholine-4-carbonyl)benzoic acid |
| 6A | 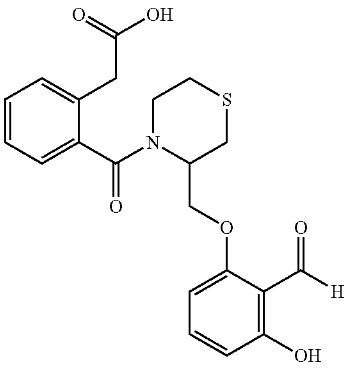 [SMILES: O=Cc1c(O)cccc1OCC1CSCCN1C(=O)c1ccccc1CC(=O)O] | 2-(2-{3-[(2-formyl-3-hydroxyphenoxy)methyl] thiomorpholine-4-carbonyl}phenyl)acetic acid |
| 7A | 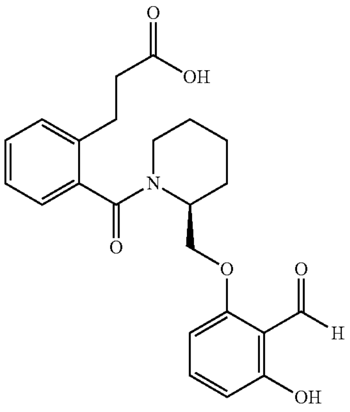 [SMILES: O=Cc1c(O)cccc1OC[C@@H]1CCCCN1C(=O)c1ccccc1CCC(=O)O] | 3-{2-[(2S)-2-[(2-formyl-3-hydroxyphenoxy)methyl]piperidine-1-carbonyl]phenyl}propanoic acid |

TABLE 1-continued

| Compound Number | Structure | IUPAC name |
|---|---|---|
| 8A | 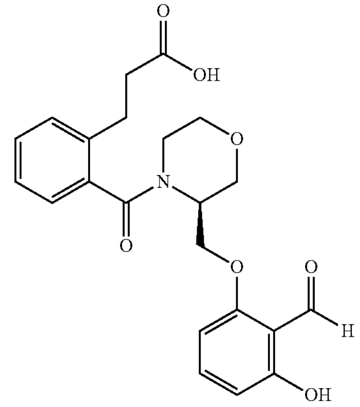 [SMILES: O=Cc1c(O)cccc1OC[C@@H]1COCCN1C(=O)c1ccccc1CCC(=O)O] | 3-{2-[(3S)-3-[(2-formyl-3-hydroxyphenoxy)methyl]morpholine-4-carbonyl]phenyl} propanoic acid |
| 9A | 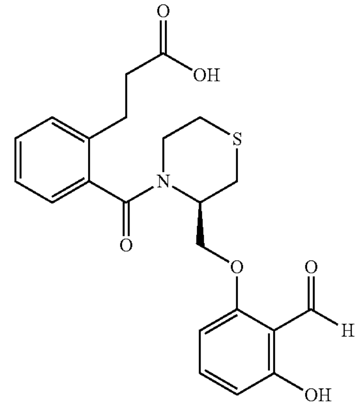 | 3-{2-[(3R)-3-[(2-formyl-3-hydroxyphenoxy)methyl] thiomorpholine-4-carbonyl]phenyl}propanoic acid |
| 1B | 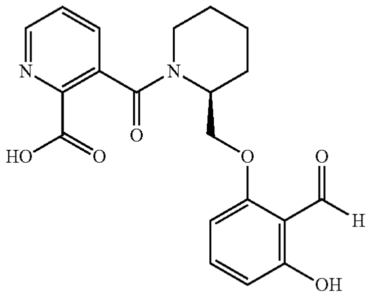 | 3-[(2S)-2-[(2-formyl-3-hydroxyphenoxy)methyl]piperidine-1-carbonyl]pyridine-2-carboxylic acid |
| 2B (Enantiomer 1) | 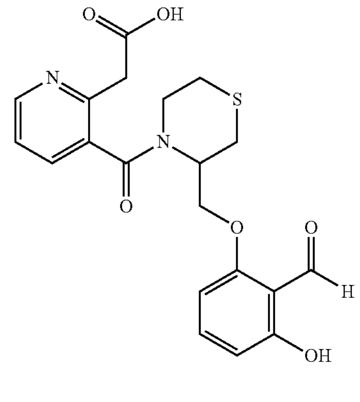 | 2-{3-[3-[(2-formyl-3-hydroxyphenoxy)methyl] thiomorpholine-4-carbonyl]pyridin-2-yl} acetic acid |

TABLE 1-continued

| Compound Number | Structure | IUPAC name |
|---|---|---|
| 3B | 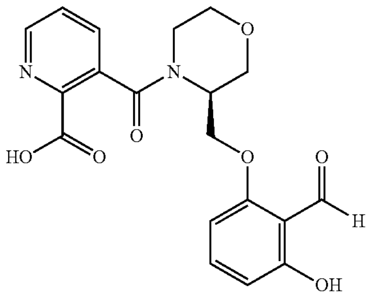 [SMILES: O=Cc1c(O)cccc1OC[C@@H]1COCCN1C(=O)c1cccnc1C(=O)O] | 3-[(3S)-3-[(2-formyl-3-hydroxyphenoxy)methyl]morpholine-4-carbonyl]pyridine-2-carboxylic acid |
| 4B | 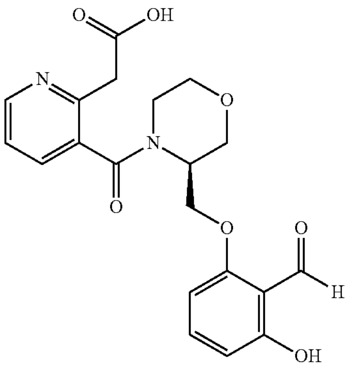 | 2-{3-[(3S)-3-[(2-formyl-3-hydroxyphenoxy)methyl]morpholine-4-carbonyl]pyridin-2-yl} acetic acid |
| 5B | 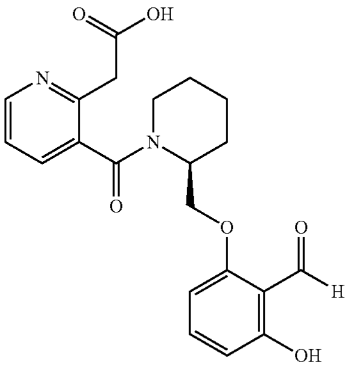 | (S)-2-(3-(2-((2-formyl-3-hydroxyphenoxy)methyl)piperidine-1-carbonyl)pyridin-2-yl)acetic acid |
| 6B (Enantiomer 1) | 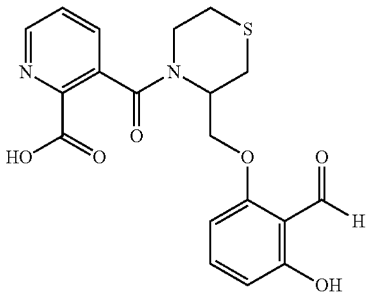 [SMILES: O=Cc1c(O)cccc1OCC1CSCCN1C(=O)c1cccnc1C(=O)O] | 3-[3-[(2-formyl-3-hydroxyphenoxy)methyl] thiomorpholine-4-carbonyl]pyridine-2-carboxylic acid |

TABLE 2

| Structure |
|---|
| 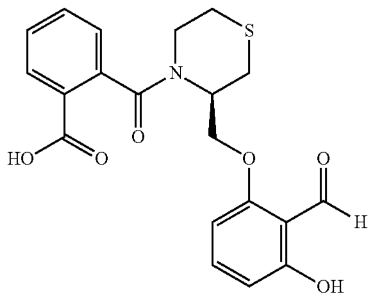 [SMILES: O=Cc1c(O)cccc1OC[C@@H]1CSCCN1C(=O)c1ccccc1C(=O)O] |
| 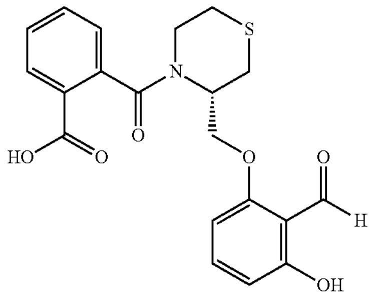 |
| 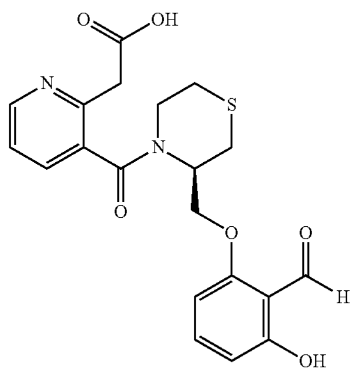 |
| 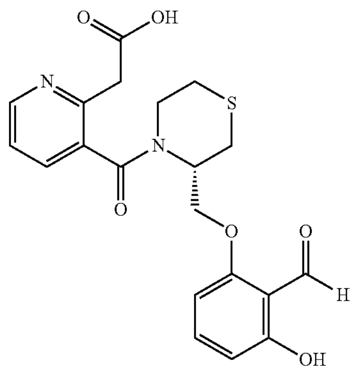 |

TABLE 2-continued

| Structure |
|---|
| 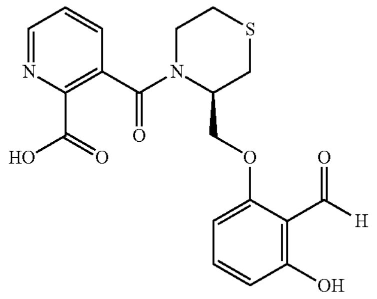 |
| 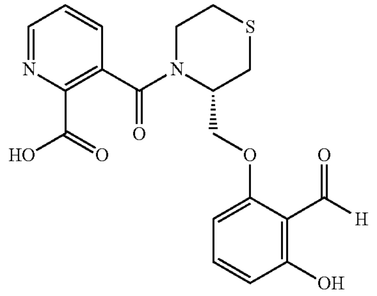 |

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease.

The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals.

Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The term "hemoglobin" as used herein refers to any hemoglobin protein, including normal hemoglobin (HbA) and abnormal hemoglobin, such as sickle hemoglobin (HbS).

The term "sickle cell disease" refers to diseases mediated by sickle hemoglobin (HbS) that results from a single point mutation in the hemoglobin (Hb). Sickle cell diseases include sickle cell anemia (HbSS), hemoglobin SC disease (HbSC), hemoglobin S beta-plus-thalassemia (HbS/β+) and hemoglobin S beta-zero-thalassemia (HbS/β0).

Provided herein are methods for treating sickle cell disease (SCD). Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels. It is contemplated that an approach to therapy would be to maintain the HbS in the oxygenated state, as polymerization occurs only in the deoxygenated state under hypoxic conditions.

In some embodiments, provided herein is a method for increasing oxygen affinity of hemoglobin S in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for increasing oxygen affinity of hemoglobin S in a subject in need thereof, comprising administering to the subject a compound as described herein or a pharmaceutical composition as described herein.

In some embodiments, provided herein is a method for treating a disorder mediated by hemoglobin in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for treating a disorder mediated by hemoglobin in a subject in need thereof, comprising administering to the subject a compound as described herein or a pharmaceutical composition as described herein. In some embodiments, the disorder is a hemoglobinopathy.

In some embodiments, the hemoglobin is sickle hemoglobin.

In some embodiments, provided herein is a method for treating sickle cell disease in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for treating sickle cell disease in a subject in need thereof, comprising administering to the subject a compound as described herein or a pharmaceutical composition as described herein.

Pharmaceutical Compositions and Modes of Administration

Compounds provided herein are usually administered in the form of pharmaceutical compositions. Thus, provided herein are also pharmaceutical compositions that comprise one or more of the compounds described herein or an isotopically enriched analog, stereoisomer, mixture of stereoisomers, or prodrug thereof, or a pharmaceutically acceptable salt of each thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modem Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or an isotopically enriched analog, stereoisomer, mixture of stereoisomers, or prodrug thereof, or a pharmaceutically acceptable salt of each thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or an isotopically enriched analog, stereoisomer, mixture of stereoisomers, or prodrug thereof, or a pharmaceutically acceptable salt of each thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or an isotopically enriched analog, stereoisomer, mixture of stereoisomers, or prodrug thereof, or a pharmaceutically acceptable salt of each thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

In some embodiments, a compound of formula I, II, or III can be synthesized by exemplary synthetic pathways as shown in Scheme A or Scheme B.

In some embodiments of Scheme A, $R^a$ can be a $C_{1-6}$ alkyl; Z can be a hydroxy protecting group or H; and X and n are as described herein. As shown in Scheme A, in embodiments wherein Z is a hydroxy protecting group, compound A1 and compound A2 are coupled first utilizing standard coupling conditions, and the protecting group subsequently cleaved under standard deprotection conditions to give compound A3. In embodiments wherein Z is H, compound A1 and compound A2 are coupled utilizing standard coupling conditions to give compound A3. In Step 2, Compound A3 can be then assembled onto 2,6-dihydroxybenzaldehyde A4 to produce compound A5. Hydrolyzing esterified compound A5 under standard conditions provides a compound of formula II.

Scheme A

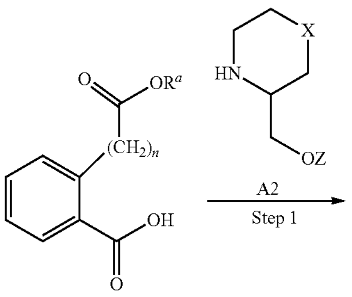

A1

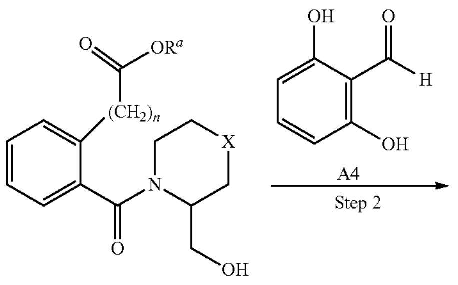

A3

-continued

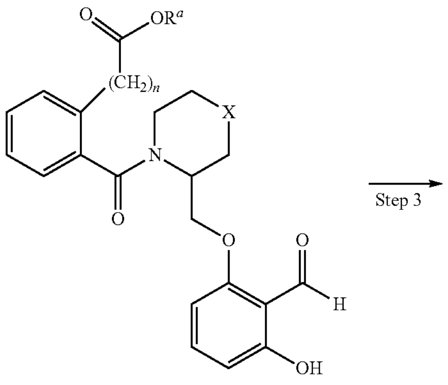

A5

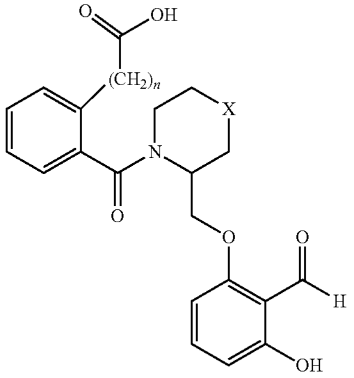

II

In some embodiments of Scheme B, $R^a$ can be a $C_{1-6}$ alkyl; Z can be a hydroxy protecting group or H; and X and n are as described herein. As shown in Scheme B, in embodiments wherein Z is a hydroxy protecting group, compound B1 and compound B2 are coupled first utilizing standard coupling conditions, and the protecting group subsequently cleaved under standard deprotection conditions to give compound B3. In embodiments wherein Z is H, compound B1 and compound B2 are coupled utilizing standard coupling conditions to give compound B3. In Step 2, Compound B3 can be then assembled onto 2,6-dihydroxybenzaldehyde B4 to produce compound B5. Hydrolyzing esterified compound B5 under standard conditions provides a compound of formula III.

Scheme B

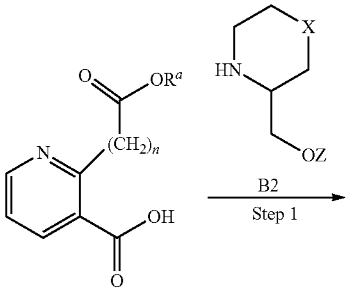

B1

-continued

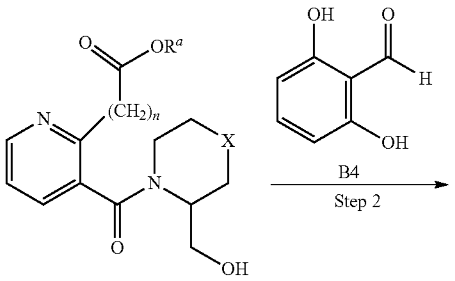

B3

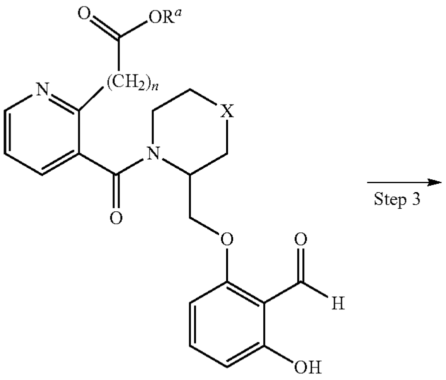

B5

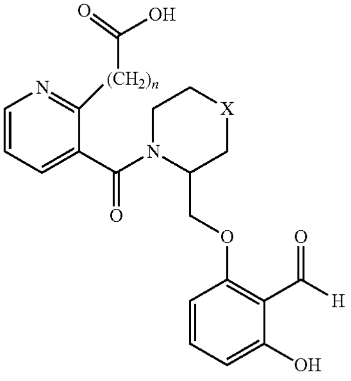

III

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Synthetic Examples

Example 1. Synthesis of 2-[(2S)-2-[(2-formyl-3-hydroxyphenoxy)methyl]piperidine-1l-carbonyl] benzoic acid, Compound 1A Compound 1A was synthesized according to Scheme 1.

Scheme 1

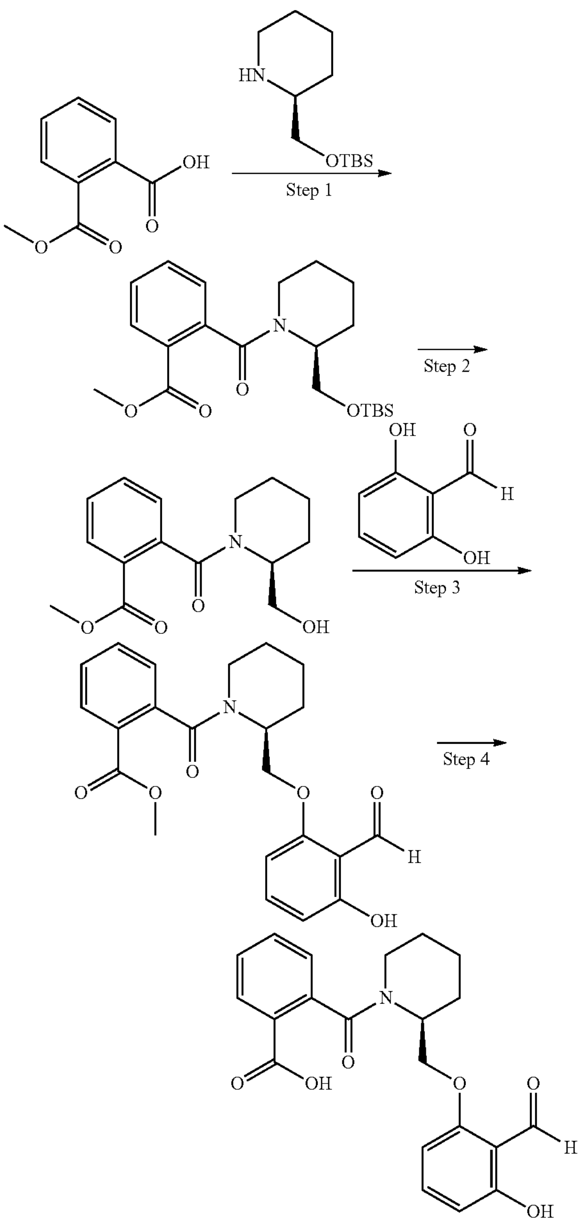

1A

Step 1

To a 250-mL round-bottom flask was placed 2-(methoxycarbonyl)benzoic acid (3.00 g, 16.652 mmol, 1.00 equiv), tetrahydrofuran (60 mL), (2S)-2-[[(tert-butyldimethylsilyl)oxy]methyl]piperidine (3.82 g, 16.652 mmol, 1.00 equiv), HATU (9.50 g, 24.978 mmol, 1.50 equiv) and DIEA (6.46 g, 49.956 mmol, 3.00 equiv). The resulting solution was stirred for 3 hr at 25° C. The resulting mixture was concentrated.

The residue was applied onto a silica gel column with ethyl acetate/petroleum ether (1:3) as eluents. This resulted in methyl 2-[(2S)-2-[[(tert-butyldimethylsilyl)oxy]methyl]piperidine-1-carbonyl]benzoate. LCMS (ES) $[M+1]^+$ m/z 392.0.

Step 2

Into a 100-mL round-bottom flask was placed methyl 2-[(2S)-2-[[(tert-butyldimethylsilyl)oxy]methyl]piperidine-1-carbonyl]benzoate (4.00 g, 10.215 mmol, 1.00 equiv), tetrahydrofuran (50 mL) and TBAF (1.34 g, 5.107 mmol, 0.50 equiv). The resulting solution was stirred for 2 hr at 25° C. The resulting mixture was then concentrated, and the residue was applied onto a silica gel column with ethyl acetate/petroleum ether (1:1) as eluents. This resulted in methyl 2-[(2S)-2-(hydroxymethyl)piperidine-1-carbonyl] benzoate. LCMS (ES) $[M+1]^+$ m/z 278.1.

Step 3

Into a 100-mL round-bottom flask was placed methyl 2-[(2S)-2-(hydroxymethyl)piperidine-1-carbonyl]benzoate (1.20 g, 4.327 mmol, 1.00 equiv), tetrahydrofuran (20 mL), 2,6-dihydroxybenzaldehyde (0.72 g, 5.193 mmol, 1.20 equiv), $PPh_3$ (1.70 g, 6.491 mmol, 1.50 equiv) and DIAD (1.31 g, 6.491 mmol, 1.50 equiv). The resulting solution was stirred for 16 hr at 25° C. The resulting mixture was concentrated. The residue was applied onto a silica gel column with ethyl acetate/petroleum ether (1:2) as eluents. This resulted in methyl 2-[(2S)-2-(2-formyl-3-hydroxyphenoxymethyl)piperidine-1-carbonyl]benzoate. LCMS (ES) $[M+1]^+$ m/z 398.2.

Step 4

Into a 50-mL round-bottom flask was placed methyl 2-[(2S)-2-(2-formyl-3-hydroxyphenoxymethyl)piperidine-1-carbonyl]benzoate (100.00 mg, 0.25 mmol, 1.00 equiv), tetrahydrofuran (5.00 mL), water (5.00 mL) and lithium hydroxide monohydrate (21.1 mg, 0.5 mmol, 2.00 equiv). The resulting solution was stirred for 2 hr at 25° C. The pH value of the solution was adjusted to 6 with HCl (1M). The resulting mixture was concentrated. The crude reaction mixture was filtered, and the filtrate was subjected to reverse phase preparative HPLC (Prep-C18, 20-45M, 120 g, Tianjin Bonna-Agela Technologies; gradient elution of 30% MeCN in water to 40% MeCN in water over a 10 min period, where both solvents contain 0.1% FA) to provide 2-[(2S)-2-[(2-formyl-3-hydroxyphenoxy)methyl]piperidine-1-carbonyl] benzoic acid. $^1H$ NMR (300 MHz, DMSO-$d_6$, ppm) δ 13.19 (br, 1H), 11.73 (br, 1H), 10.20 (s, 1H), 7.99-7.89 (m, 1H), 7.80-6.85 (m, 4H), 6.79-6.67 (m, 1H), 6.62-6.51 (m, 1H), 5.32-4.97 (m, 1H), 4.52-3.85 (m, 2H), 3.16-2.82 (m, 2H), 2.02-1.42 (m, 6H). LCMS (ES) $[M+1]^+$ m/z 384.1.

Example 2. Synthesis of 2-[(3S)-3-[(2-formyl-3-hydroxyphenoxy)methyl]morpholine-4-carbonyl] benzoic acid, Compound 2A Compound 2A was synthesized according to Scheme 2.

Scheme 2

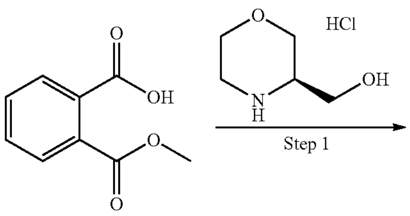

-continued

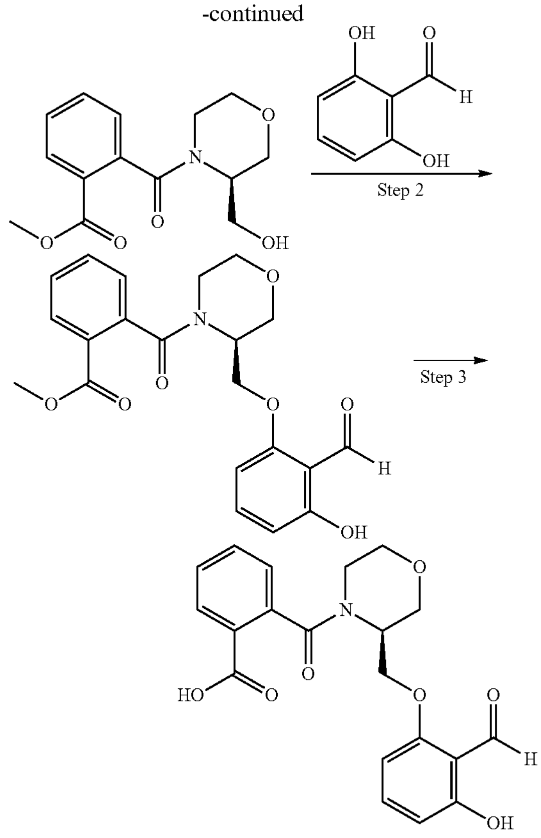

2A

Step 1

Into a 50-mL 3-necked round-bottom flask was placed 2-(methoxycarbonyl)benzoic acid (1.0 g, 5.55 mmol, 1.0 equiv), DMF (10 mL), (3R)-morpholin-3-yl-methanol hydrochloride (1.02 g, 6.64 mmol, 1.2 equiv) and DIEA (0.86 g, 6.66 mmol, 1.2 equiv). This was followed by the addition of HATU (2.53 g, 6.66 mmol, 1.2 equiv) in several batches at 0° C. The reaction solution was warmed to room temperature and stirred for 2 h. The mixture was diluted with 20 mL of water, and extracted with 3×50 mL of ethyl acetate. The combined organic phase was washed with 3×20 mL of brine, dried over anhydrous sodium sulfate, and filtered. The filtrate was concentrated under reduced pressure. The residue was purified by silica gel column with ethyl acetate/petroleum ether (60/40) as eluents. This resulted in methyl 2-[(3R)-3-(hydroxymethyl)morpholine-4-carbonyl]benzoate. LCMS (ES) [M+1]+m/z: 280.

Step 2

Into a 100-mL 3-necked round-bottom flask was placed methyl 2-[(3R)-3-(hydroxymethyl)morpholine-4-carbonyl] benzoate (900 mg, 3.22 mmol, 1.0 equiv), THF (50 mL), 2,6-dihydroxybenzaldehyde (534 mg, 3.87 mmol, 1.2 equiv) and $PPh_3$ (1.01 g, 3.87 mmol, 1.2 equiv). This was followed by the addition of a solution of DIAD (782 mg, 3.87 mmol, 1.2 equiv) in THF (2 mL) dropwise with stirring at 0° C. After addition, the mixture was stirred overnight at room temperature. The mixture was concentrated to remove the solvent, and the residue was purified by silica gel column with ethyl acetate/petroleum ether (1:2). This resulted in methyl 2-[(3S)-3-(2-formyl-3-hydroxyphenoxymethyl)morpholine-4-carbonyl]benzoate. LCMS (ES) $[M+1]^+$ m/z: 400.

Step 3

Into a 50-mL round-bottom flask was placed methyl 2-[(3S)-3-(2-formyl-3-hydroxyphenoxymethyl)morpholine-4-carbonyl]benzoate (360 mg, 0.90 mmol, 1.0 equiv) and THF (10 mL). This was followed by the addition of a solution of $LiOH \cdot H_2O$ (76 mg, 1.80 mmol, 2.0 equiv) in $H_2O$ (20 mL) dropwise with stirring at 0° C. The mixture was stirred for 2 h at room temperature. The resulting solution was extracted with 30 mL of ethyl acetate and the aqueous layers combined. The pH value of the solution was adjusted to 4-5 with HCl (1M) and extracted with 3×30 mL of dichloromethane. The combined organic phase was concentrated under reduced pressure. The crude product was purified by Flash-Prep-HPLC with the following conditions: Column: Ascentis Express C18, 50×3.0 mm, 2.7 μm, Mobile Phase A: Water/0.05% FA, Mobile Phase B: MeCN, Flow rate: 1.5 mL/min, Gradient: 5% B to 100% B in 1.2 min, hold 0.6 min. This resulted in 2-[(3S)-3-[(2-formyl-3-hydroxyphenoxy)methyl]morpholine-4-carbonyl]benzoic acid. $^1$H-NMR: (300 MHz, DMSO-$d_6$, ppm): δ 13.30 (br, 1H), 11.80 (s, 1H), 10.32 (s, 1H), 8.14-7.39 (m, 5H), 6.75-6.49 (m, 2H), 4.75-4.26 (m, 3H), 4.15-3.37 (m, 4H), 3.32-2.94 (m, 2H). LCMS: (ES, m/z): $[M+H]^+$: 386.

Example 3. Synthesis of 2-{2-[(3S)-3-[(2-formyl-3-hydroxyphenoxy)methyl]morpholine-4-carbonyl]phenyl}acetic acid, Compound 3A Compound 3A was synthesized according to Scheme 3.

Scheme 3

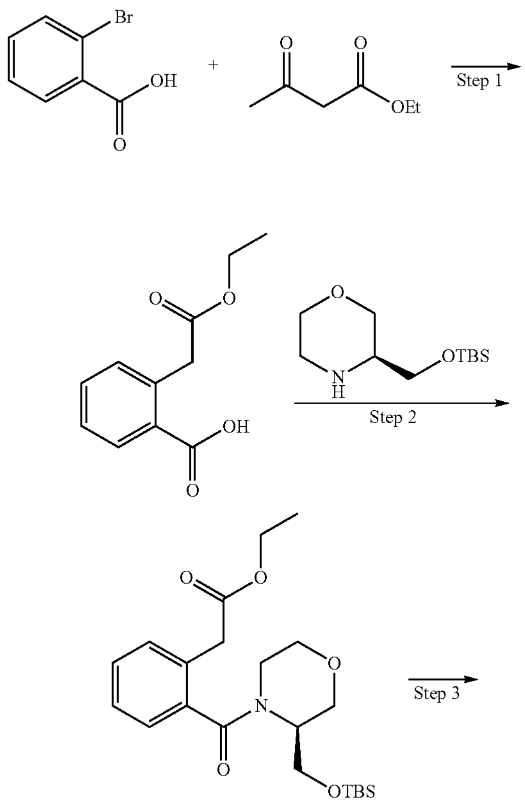

-continued

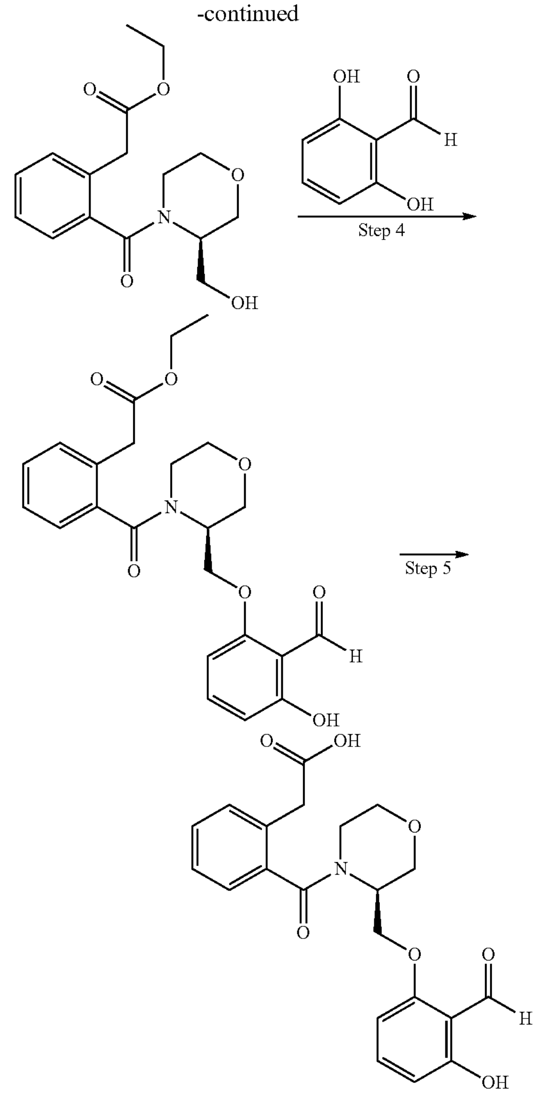

3A

Step 1

Into a 250-mL round-bottom flask was placed EtOH (70.00 mL), NaOEt (3.05 g, 44.8 mmol, 3.00 equiv) and ethyl acetoacetate (3.88 g, 29.85 mmol, 2.00 equiv). After the mixture was stirred 10 min at room temperature, CuBr (428.2 mg, 2.99 mmol, 0.20 equiv) and ortho-bromobenzoic acid (3.00 g, 14.9 mmol, 1.0 equiv) was added. The reaction solution was heated to reflux for 2 hr in an oil bath. The resulting mixture was concentrated and diluted with 50 mL of HCl (1M). The resulting solution was extracted with 3×40 mL of ethyl acetate, dried over anhydrous sodium sulfate, and concentrated. The residue was applied onto a silica gel column with petroleum ether/ethyl acetate (100:0 to 82:28). This resulted in 2-(2-ethoxy-2-oxoethyl)benzoic acid. LCMS: (ES, m/z): $[M+H]^+$: 209.1.

Step 2

Into a 50-mL round-bottom flask was placed 2-(2-ethoxy-2-oxoethyl)benzoic acid (500 mg, 2.4 mmol, 1.00 equiv), DMF (20 mL), HATU (1.1 g, 2.9 mmol, 1.20 equiv), DIEA (621 mg, 4.8 mmol, 2.00 equiv) and (3S)-3-(((tert-butyldimethylsilyl)oxy)methyl)morpholine (556 mg, 2.4 mmol, 1.00 equiv). The resulting solution was stirred overnight at room temperature. The reaction was then quenched by the addition of 30 mL of water. The resulting solution was extracted with 2×60 mL of ethyl acetate. The organic phase was combined, washed with water (2×60 mL), dried over anhydrous sodium sulfate and concentrated. The residue was applied onto a silica gel column with petroleum ether/THF (100:0 to 92:8). This resulted in ethyl (S)-2-(2-(3-(((tert-butyldimethylsilyl)oxy)methyl)morpholine-4-carbonyl)-phenyl)acetate. LCMS: (ES, m/z): $[M+H]^+$: 422.2.

Step 3

Into a 50-mL round-bottom flask was placed ethyl (S)-2-(2-(3-(((tert-butyldimethylsilyl)oxy)methyl)morpholine-4-carbonyl)-phenyl)acetate (0.90 g, 2.14 mmol, 1.00 equiv), THF (20 mL) and TBAF(1M, THF) (0.43 mL, 0.43 mmol, 0.20 equiv). The resulting solution was stirred for 2 hr at room temperature. The mixture was concentrated and applied onto a silica gel column with petroleum ether/THF (100:0 to 80:20) as eluents. This resulted in ethyl (R)-2-(2-(3-(hydroxymethyl)morpholine-4-carbonyl)phenyl)acetate. LCMS (ES, m/z): $[M+H]^+$: 308.1.

Step 4

Into a 50-mL 3-necked round-bottom flask purged and maintained with an inert atmosphere of nitrogen was placed ethyl (R)-2-(2-(3-(hydroxymethyl)morpholine-4-carbonyl) phenyl)acetate (0.30 g, 0.98 mmol, 1.00 equiv), 2,6-dihydroxybenzaldehyde (175 mg, 1.27 mmol, 1.30 equiv), $PPh_3$ (384 mg, 1.5 mmol, 1.50 equiv) and THF (20 mL). Then, DIAD (237 mg, 1.17 mmol, 1.20 equiv) was added dropwise at 0° C. The reaction solution was stirred overnight at room temperature. The resulting mixture was concentrated. The residue was applied onto a silica gel column with petroleum ether/ethyl acetate (100:0 to 70:30) as eluents. This resulted in ethyl (S)-2-(2-(3-((2-formyl-3-hydroxyphenoxy)methyl) morpholine-4-carbonyl)-phenyl)acetate. LCMS (ES, m/z): $[M+H]^+$: 428.2.

Step 5

Into a 50-mL round-bottom flask was placed ethyl (S)-2-(2-(3-((2-formyl-3-hydroxyphenoxy)methyl)morpholine-4-carbonyl)-phenyl)acetate (250 mg, 0.56 mmol, 1.00 equiv) and THF (8 mL). A solution of LiOH (28 mg, 1.17 mmol, 2.00 equiv) in water (8 mL) was added. The resulting solution was stirred for 2 hr at room temperature. The solution was diluted with 20 mL of water and extracted with 20 mL of ethyl acetate. The pH value of the aqueous phase was adjusted to 5-6 with HCl (1M), extracted with 3×20 mL of dichloromethane, dried over $Na_2SO_4$ and concentrated. The crude product was purified by Prep-HPLC with the following conditions: Column, X-Bridge prep phenyl OBD column 19×150. mobile phase, phase A water(0.05% FA), phase B, MeCN; Gradient, 22% B up to 60% in 10 min; Flow rate, 20 mL/min. Detector, 220 nm. This resulted in 2-(2-((3S)-3-((2-formyl-3-hydroxyphenoxy)methyl)morpholine-4-carbonyl)phenyl)acetic acid. $^1$H-NMR 300 MHz, DMSO-d6, ppm): δ 12.50 (br, 1H), 12.35 (br, 1H), 10.26 (s, 1H), 7.59-7.08 (m, 5H), 6.80-6.54 (m, 2H), 5.08-4.80 (m, 1H), 4.57-4.02 (m, 3H), 3.92-3.12 (m, 7H). LCMS: (ES, m z): $[M+H]^+$: 400.1.

Example 4. Synthesis of 2-{2-[(2S)-2-[(2-formyl-3-hydroxyphenoxy)methyl]piperidine-1-carbonyl] phenyl}acetic acid, Compound 4A Compound 4A was synthesized according to Scheme 4.

Scheme 4

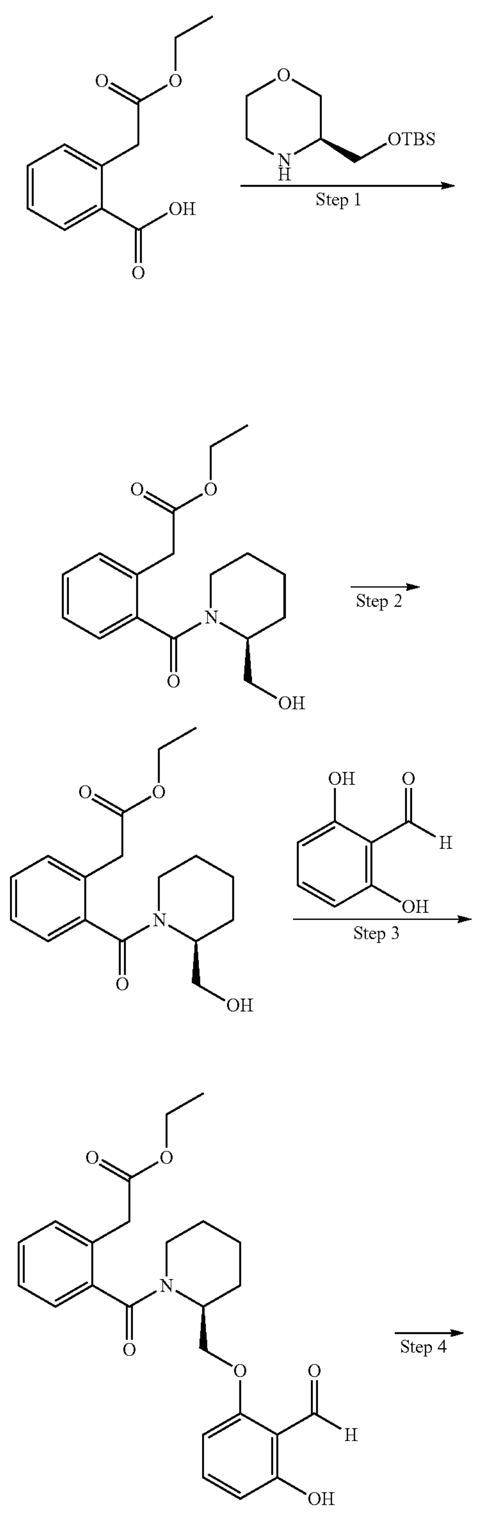

-continued

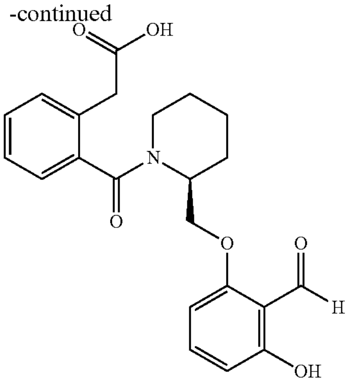

4A

Step 1

Into a 100-mL 3-necked round-bottom flask was placed 2-(2-ethoxy-2-oxoethyl)benzoic acid (400 mg, 1.92 mmol, 1.00 equiv), (2S)-2-[[(tert-butyldimethylsilyl)oxy]methyl]piperidine (661 mg, 2.88 mmol, 1.50 equiv), DIPEA (372 mg, 2.88 mmol, 1.50 equiv) and DMF (10.0 mL). The reaction was cooled to 0° C. and HATU (1.09 g, 2.88 mmol, 1.50 equiv) was added in portions. The resulting solution was stirred for 16 hr at 0-25° C. and quenched by the addition of 30 mL of water. The resulting solution was extracted with ethyl acetate (4×30 mL), and the combined organic layers were washed with brine, dried over anhydrous sodium sulfate, and concentrated under vacuum. The residue was applied onto a silica gel column with ethyl acetate/petroleum ether (1:50 to 1:5) as eluents. This resulted in ethyl 2-[2-[(2S)-2-[[(tert-butyldimethylsilyl) oxy]methyl]piperidine-1-carbonyl]phenyl]acetate. LCMS (ES) [M+1]+ m/z: 420.2.

Step 2

Into a 50-mL round-bottom flask was placed ethyl 2-[2-[(2S)-2-[[(tert-butyldimethylsilyl)oxy]methyl]piperidine-1-carbonyl]phenyl]acetate (660 mg, 1.57 mmol, 1.00 equiv), dioxane (3.0 mL) and HCl in 1,4-dioxane (0.78 mL, 1.57 mmol, 2.00 equiv, 2.0 M) at 0° C. The resulting solution was stirred for 2 hr at 0-20° C. The pH value of the solution was adjusted to 8 with saturated $NaHCO_3$. The resulting solution was extracted with 3×10 mL of ethyl acetate, and the organic layers combined, dried over anhydrous sodium sulfate, and concentrated. This resulted in ethyl 2-[2-[(2S)-2-(hydroxymethyl)piperidine-1-carbonyl]phenyl]acetate. LCMS (ES) $[M+1]^+$ m/z: 306.1.

Step 3

Into a 100-mL 3-necked round-bottom flask purged and maintained with an inert atmosphere of nitrogen was placed ethyl 2-[2-[(2S)-2-(hydroxymethyl)piperidine-1-carbonyl]phenyl]acetate (250 mg, 0.819 mmol, 1.00 equiv), 2,6-dihydroxybenzaldehyde (141 mg, 1.02 mmol, 1.25 equiv), $PPh_3$ (322 mg, 1.23 mmol, 1.50 equiv) and DCM (15. 0 mL). The reaction was cooled to 0° C. and a solution of DBAD (282 mg, 1.22 mmol, 1.50 equiv) in DCM (2.0 mL) was added dropwise. The resulting solution was stirred for 16 hr at 0-25° C. The resulting mixture was concentrated. The residue was applied onto a silica gel column with ethyl acetate/petroleum ether (1:100 to 1:10) as eluents. This resulted in ethyl 2-[2-[(2S)-2-(2-formyl-3-hydroxyphenoxymethyl)piperidine-1-carbonyl]phenyl]acetate. LCMS (ES) $[M+1]^+$ m/z: 426.2.

Step 4

Into a 100-mL round-bottom flask was placed ethyl 2-[2-[(2S)-2-(2-formyl-3-hydroxyphenoxymethyl)piperidine-1-carbonyl]phenyl]acetate (260 mg, 0.611 mmol, 1.00 equiv) and THF (5.0 mL). After the reaction was cooled to 0° C., a solution of NaOH (122 mg, 3.05 mmol, 5.00 equiv) in $H_2O$ (5.0 mL) was added dropwise. The resulting solution was stirred for 2 hr at 0-25° C. The pH value of the solution was adjusted to 6 with HCl (2M). The resulting solution was extracted with 3×15 mL of ethyl acetate, and the organic layers were combined, dried over $Na_2SO_4$ and concentrated. The crude product was purified by Flash-Prep-HPLC with the following conditions (IntelFlash-1): Column, XBridge Prep C18 OBD Column, 19 cm, 150 mm, 5 μm; mobile phase, Water (0.1% HCOOH) and MeCN (30% Phase B up to 40% in 10 min); Detector, 254 nm. This resulted in 2-{2-[(2S)-2-[(2-formyl-3-hydroxyphenoxy)methyl]piperidine-1-carbonyl]phenyl}acetic acid. $^1H$ NMR (300 MHz, DMSO-$d_6$, ppm) δ 12.20 (br, 1H), 11.97 (br, H), 10.31-10.21 (m, 1H), 7.58-7.28 (m, 5H), 6.95-6.74 (m, 1H), 6.53 (d, J=8.4 Hz, 1H), 5.22-5.12 (m, 1H), 4.52-4.26 (m, 2H), 3.79-2.74 (m, 4H), 1.92-1.41 (m, 6H). LCMS (ES) $[M+1]^+$ m/z: 398.1.

Example 5. Synthesis of 2-(3-((2-formyl-3-hydroxyphenoxy)methyl)thiomorpholine-4-carbonyl) benzoic acid, Compound 5A (Enantiomer 1)

Compound 5A, Enantiomer 1 was synthesized according to Scheme 5.

Scheme 5

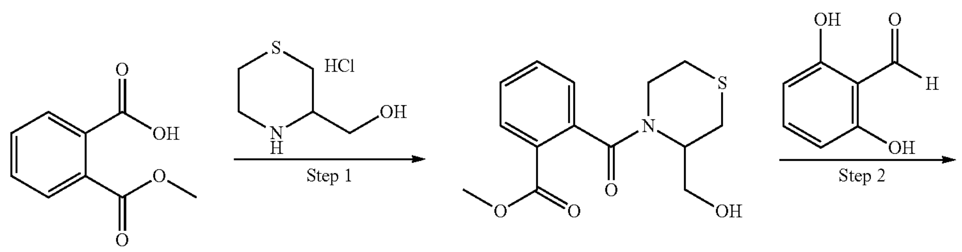

-continued

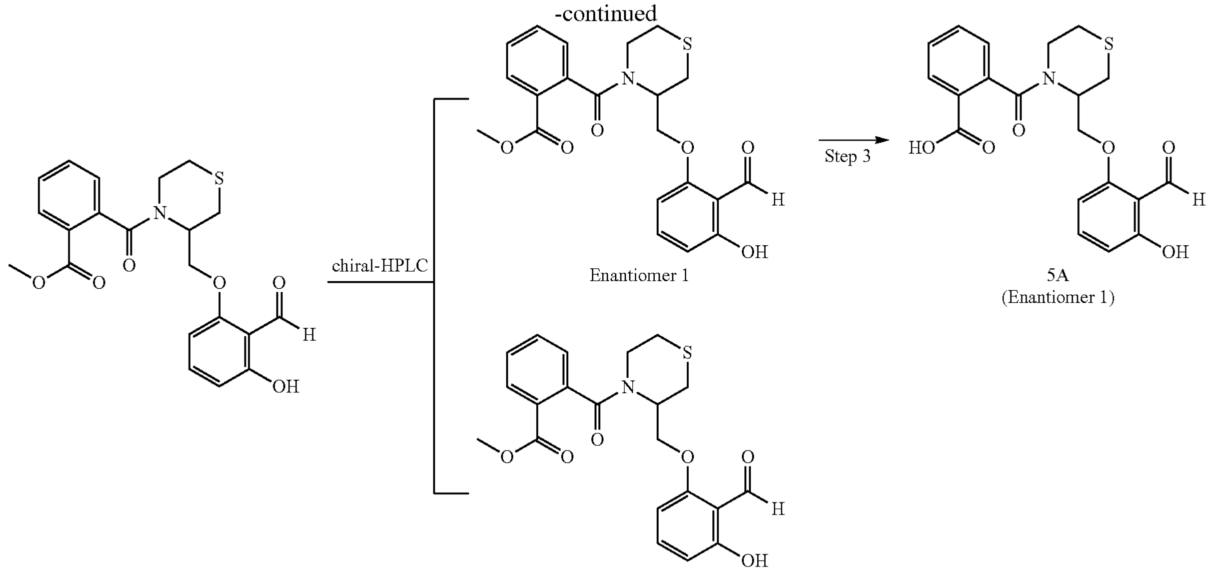

Enantiomer 1

Enantiomer 2

5A
(Enantiomer 1)

Step 1

Into a 50-mL round-bottom flask was placed 2-(methoxycarbonyl)benzoic acid (1.20 g, 6.66 mmol, 1.0 equiv), thiomorpholin-3-yl-methanol hydrochloride (1.24 g, 7.31 mmol, 1.1 equiv), DMF (20 mL) and DIEA (2.58 g, 19.96 mmol, 3.0 equiv). This was followed by addition of HATU (3.00 g, 7.89 mmol, 1.2 equiv) in three batches at 0° C. After addition, the reaction solution was stirred for 2 h at room temperature. The reaction was then quenched by the addition of water (30 mL) and extracted with 3x30 mL of ethyl acetate. The combined organic phase was washed with brine (3x30 mL), dried over anhydrous sodium sulfate, and filtered. The filtrate was concentrated under reduced pressure, and the residue was purified by silica gel column with ethyl acetate/petroleum ether (1/2) as eluents. This resulted in methyl 2-(3-(hydroxymethyl)thiomorpholine-4-carbonyl) benzoate. LCMS (ES) [M+1]+m/z: 296.

Step 2

Into a 250-mL 3-necked round-bottom flask purged and maintained with an inert atmosphere of nitrogen was placed methyl 2-[3-(hydroxymethyl)thiomorpholine-4-carbonyl] benzoate (1.75 g, 5.93 mmol, 1.0 equiv), 2,6-dihydroxybenzaldehyde (977 mg, 7.07 mmol, 1.2 equiv), $PPh_3$ (1.85 g, 7.05 mmol, 1.2 equiv), and THF (100 mL). This was followed by the addition of DBAD (1.63 g, 7.08 mmol, 1.2 equiv) at 0° C. The reaction solution was stirred overnight at room temperature. The mixture was concentrated to remove the solvent, the residue was purified by silica gel column with ethyl acetate/petroleum ether (1/1) to give racemic product.

The racemate was further purified by Chiral-HPLC with conditions: Column: CHIRALPAK IG-3 30*250 mm, 5 μm, Mobile phase: A: Methanol B: Ethanol, Flow rate: 20 mL/min, Gradient: 50% B in 25 min, detector, 220 nm. This resulted in methyl 2-(3-((2-formyl-3-hydroxyphenoxy) methyl)thiomorpholine-4-carbonyl)benzoate, Enantiomer 1 (retention time=25 min; LCMS (ES) $[M+1]^+$ m/z: 416) and methyl 2-(3-((2-formyl-3-hydroxyphenoxy)methyl)thiomorpholine-4-carbonyl)benzoate, Enantiomer 2 (retention time=29 min; LCMS (ES) $[M+1]^+$ m/z: 416).

Step 3

Into a 25-mL vial, was placed methyl 2-(3-((2-formyl-3-hydroxyphenoxy)methyl)thiomorpholine-4-carbonyl)benzoate, Enantiomer 1 (200 mg, 0.48 mmol, 1.0 equiv), $H_2O$/MeOH=2/1 (6.0 mL) and NaOH (58 mg, 1.44 mmol, 3.0 equiv). The mixture was stirred for 1.5 h at 50° C. After cooling to room temperature, the pH value of the solution was adjusted to 5 with 2N HCl and extracted with DCM (2x50 mL). The solution was concentrated to remove the solvent, and the crude product was purified by Prep-HPLC with the following conditions: Column, Welch XB-C18, 21.2x250 mm, 5 μm, mobile phase, Water (0.1% FA) and MeCN (30% Phase B up to 70% in 12 min), Detector, 254 nm and analyzed by SFC chiral analysis: Cosolvent: MeOH, Conc. of Phase B: 10.0%, Flow Rate: 1.500 mL/min. This resulted in Compound 5A, Enantiomer 1. SFC retention time=2.88 min. $^1$H-NMR (300 MHz, DMSO-$d_6$, ppm): δ 13.38 (br, 1H), 11.71 (br, 1H), 10.31 (s, 1H), 7.97-7.93 (m, 1H), 7.66-7.12 (m, 4H), 6.74-6.51 (m, 2H), 5.41-3.99 (m, 3H), 3.37-2.33 (m, 6H). LCMS: (ES, m/z): $[M+H]^+$: 402.1.

Example 6. Synthesis of 2-(3-((2-formyl-3-hydroxyphenoxy)methyl)thiomorpholine-4-carbonyl) benzoic acid, Compound 5A (Enantiomer 2)

Compound 5A, Enantiomer 2 was synthesized according to Scheme 6.

Scheme 6

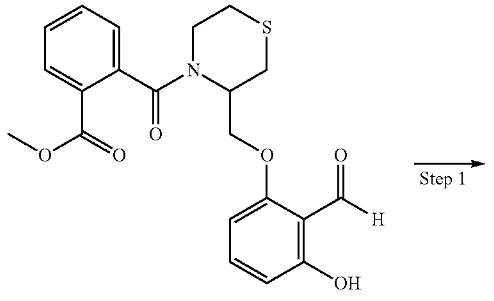

-continued

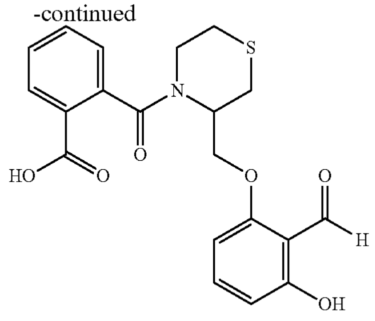

5A
(Enantiomer 2)

Step 1

Into a 25-mL vial was placed methyl 2-(3-((2-formyl-3-hydroxyphenoxy)methyl)thiomorpholine-4-carbonyl)benzoate, Enantiomer 2 (200 mg, 0.48 mmol, 1.0 equiv), $H_2O$/MeOH=2/1 (6.0 mL) and NaOH (58 mg, 1.44 mmol, 3.0 equiv). The mixture was stirred for 1.5 h at 50° C. After cooling to room temperature, the pH value of the solution was adjusted to 5 with 2N HCl and extracted with DCM (2×50 mL). The organic layers were combined and concentrated to remove the solvent, and the crude product was purified by Prep-HPLC with the following conditions (2 #SHIMADZU (HPLC-01)): Column, Welch XB-C18, 21.2×250 mm, 5 μm, mobile phase, Water(0.1% FA) and MeCN (30% Phase B up to 70% in 12 min), Detector, 254 nm and analyzed by SFC chiral analysis: Cosolvent: MeOH, Conc. of Phase B: 10.0%, Flow Rate: 1.500 m/min. This resulted in Compound 5A, Enantiomer 2. $^1$H-NMR (300 MHz, DMSO-$d_6$, ppm): δ 13.38 (br, 1H), 11.71 (br, 1H), 10.31 (s, 1H), 7.97-7.93 (m, 1H), 7.66-7.12 (m, 4H), 6.74-6.51 (m, 2H), 5.41-3.99 (m, 3H), 3.37-2.33 (m, 6H). LCMS (ES, m/z): $[M+H]^+$: 402.1.

Example 7. Synthesis of 2-(2-{3-[(2-formyl-3-hydroxyphenoxy)methyl]thiomorpholine-4-carbonyl}phenyl)acetic acid, Compound 6A Compound 6A was synthesized according to Scheme 7.

Scheme 7

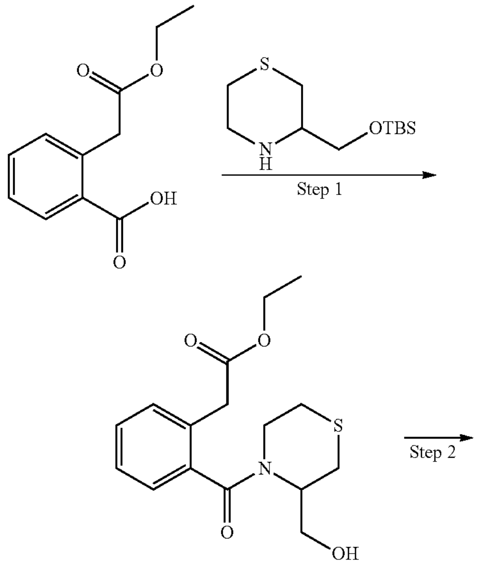

-continued

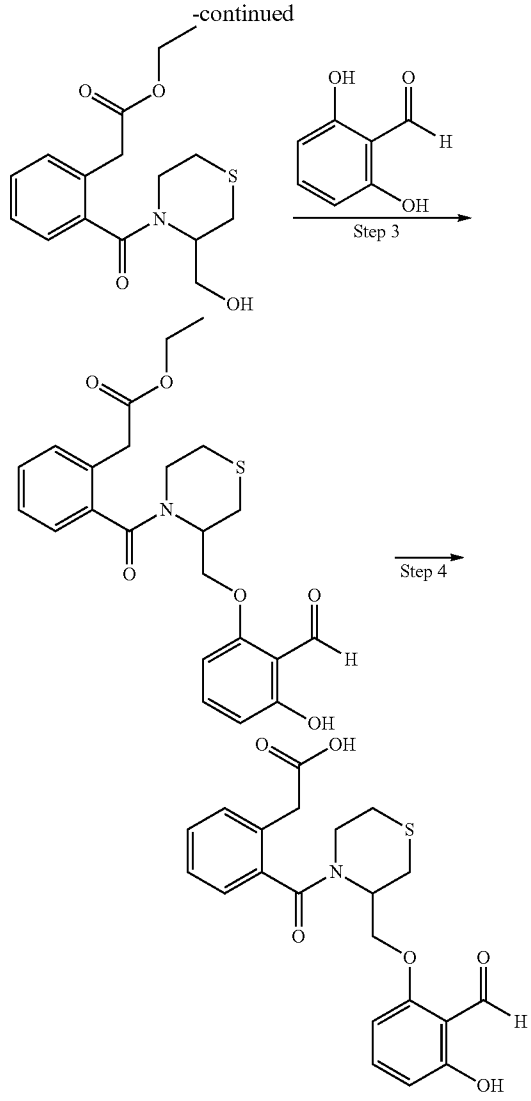

6A

Step 1

Into a 100-mL 3-necked round-bottom flask was placed 2-(2-ethoxy-2-oxoethyl)benzoic acid (400 mg, 1.92 mmol, 1.00 equiv), 3-[[(tert-butyldimethylsilyl)oxy]methyl]thiomorpholine (570 mg, 2.30 mmol, 1.20 equiv) and DMF (10.0 mL). After the reaction was cooled to 0° C., DIPEA (372 mg, 2.88 mmol, 1.50 equiv) and HATU (1.09 g, 2.88 mmol, 1.50 equiv) were added in portions. The resulting solution was stirred for 16 hr at 0-25° C. The reaction was then quenched by the addition of 30 mL of water. The resulting solution was extracted with 3×30 mL of ethyl acetate, dried over anhydrous sodium sulfate, and concentrated under vacuum. The residue was applied onto a silica gel column with ethyl acetate/petroleum ether (1:50 to 1:5) as eluents. This resulted in ethyl 2-[2-(3-[[(tert-butyldimethylsilyl)oxy]methyl]thiomorpholine-4-carbonyl)phenyl]acetate. LCMS (ES) $[M+1]^+$ m/z: 438.2.

Step 2

Into a 100-mL round-bottom flask was placed ethyl 2-[2-(3-[[(tert-butyldimethylsilyl)oxy]methyl]thiomorpholine-4-carbonyl)phenyl]acetate (600 mg, 1.37 mmol, 1.00 equiv) and ethyl acetate (3.00 mL). This was followed by the addition of HCl(gas) in ethyl acetate (2.00 mL, 4.00 mmol, 3.00 equiv, 2 M) dropwise with stirring at 0° C. The resulting solution was stirred for 2 h at room temperature. The pH value of the solution was adjusted to 8 with saturated $NaHCO_3$. The resulting solution was extracted with 3x10 mL of ethyl acetate, and the organic layers were combined, dried over anhydrous sodium sulfate, and concentrated. This resulted in ethyl 2-[2-[3-(hydroxymethyl)thiomorpholine-4-carbonyl]phenyl]acetate. LCMS (ES) $[M+1]^+$ m/z: 324.2.

Step 3

Into a 100-mL 3-necked round-bottom flask purged and maintained with an inert atmosphere of nitrogen was placed ethyl 2-[2-[3-(hydroxymethyl)thiomorpholine-4-carbonyl]phenyl]acetate (250 mg, 0.773 mmol, 1.00 equiv), DCE (5.0 mL) and TEA (391 mg, 3.86 mmol, 5.00 equiv). After the reaction was cooled to 0° C., MsCl (110 mg, 0.966 mmol, 1.25 equiv) was added dropwise. The reaction was stirred at 0-25° C. for 2 h. 2,6-dihydroxybenzaldehyde (133 mg, 0.966 mmol, 1.25 equiv) and $NaHCO_3$ (129 mg, 1.54 mmol, 2.00 equiv) were added in one portion. The resulting solution was stirred for 16 h at 55° C. The reaction was then quenched by the addition of 20 mL of water and extracted with 3x30 mL of ethyl acetate. The organic layers were combined, dried over anhydrous sodium sulfate, and concentrated under vacuum. The residue was applied onto a silica gel column with ethyl acetate/petroleum ether (1:100 to 1:20) as eluents. This resulted in ethyl 2-[2-[3-(2-formyl-3-hydroxyphenoxymethyl)thiomorpholine-4-carbonyl]phenyl]acetate. LCMS (ES) $[M+1]^+$ m/z: 444.

Step 4

Into a 100-mL 3-necked round-bottom flask was placed ethyl 2-[2-[3-(2-formyl-3-hydroxyphenoxymethyl)thiomorpholine-4-carbonyl]phenyl]acetate (100 mg, 0.225 mmol, 1.00 equiv) and THF (3.0 mL). After the reaction was cooled to 0° C., a solution of NaOH (27.1 mg, 0.676 mmol, 3.00 equiv) in $H_2O$ (3.0 mL) was added dropwise. The resulting solution was stirred for 2 hr at 0-25° C. The pH value of the solution was adjusted to 6 with HCl (2M). The resulting solution was extracted with 3x15 mL of ethyl acetate. The organic layers were combined, dried over $Na_2SO_4$, and concentrated. The crude product was purified by Flash-Prep-HPLC with the following conditions (IntelFlash-1): Column, XBridge Prep C18 OBD Column, 19 cm, 150 mm, 5 μm; mobile phase, Water (0.1% HCOOH) and MeCN (30% Phase B up to 40% in 10 min); Detector, 254 nm. This resulted in [2-[3-(2-formyl-3-hydroxyphenoxymethyl)thiomorpholine-4-carbonyl]phenyl]acetic acid. $^1H$ NMR (300 MHz, DMSO-$d_6$, ppm) δ 11.83 (br, 1H), 10.32-10.17 (m, 1H), 7.61-7.01 (m, 5H), 6.73-6.72 (m, 1H), 6.55 (d, J=8.4 Hz, 1H), 5.43-5.29 (m, 1H), 4.81-4.18 (m, 2H), 3.79-3.10 (m, 5H), 2.94-2.27 (m, 3H). LCMS (ES) $[M+1]^+$ m/z: 416.1.

Example 8. Synthesis of 3-{2-[(2S)-2-[(2-formyl-3-hydroxyphenoxy)methyl]piperidine-1-carbonyl]phenyl}propanoic acid, Compound 7A Compound 7A was synthesized according to Scheme 8.

Scheme 8

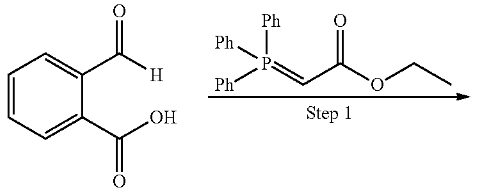

-continued

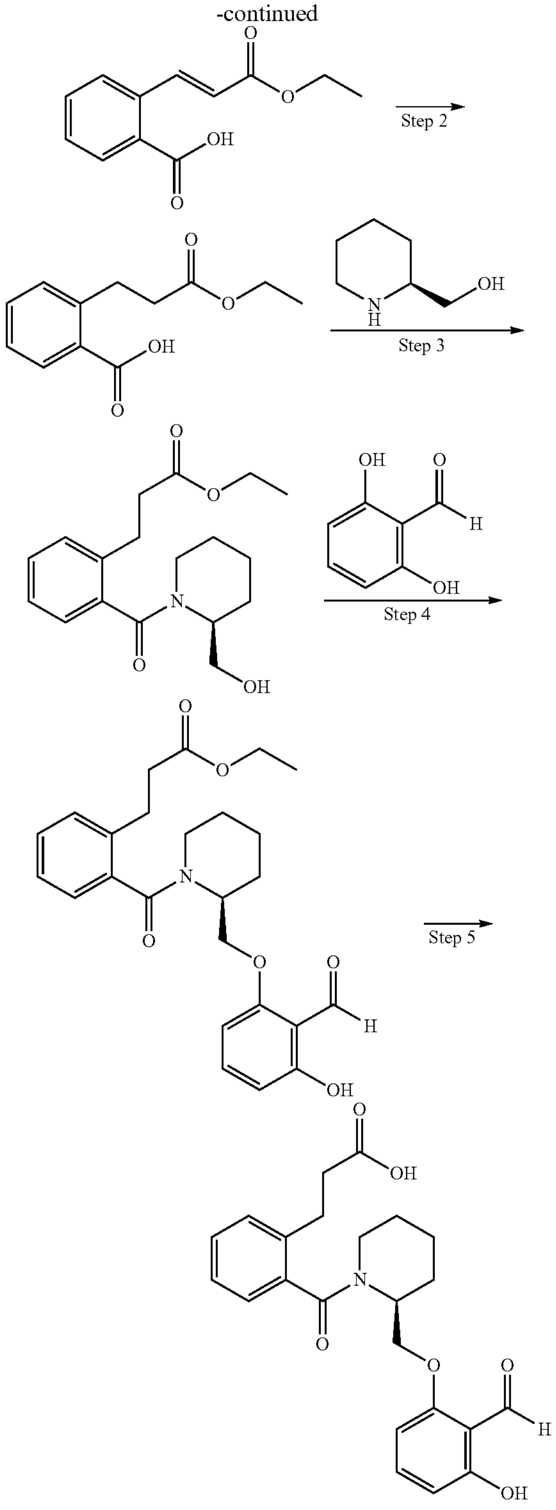

7A

Step 1

Into a 250-mL round-bottom flask was placed 2-carboxybenzaldehyde (10.0 g, 66.61 mmol, 1.00 equiv), toluene (100 mL), and (ethoxycarbonylmethylene)triphenylphosphorane (25.5 g, 73.27 mmol, 1.10 equiv). The resulting solution was stirred for 3 hr at 80° C. in an oil bath. The reaction mixture was cooled to room temperature, diluted with 50 mL of $Na_2CO_3$ (aq), and extracted with 2×100 mL of ethyl acetate. The pH value of the aqueous layers was adjusted to 4-5 with 4 M HCl and extracted with 3×100 mL of dichloromethane. The combined organic phase was dried over anhydrous sodium sulfate and filtered, and the filtrate was concentrated. This resulted in (E)-2-(3-ethoxy-3-oxoprop-1-en-1-yl)benzoic acid. LCMS (ES, m/z): $[M+H]^+$: 221.

Step 2

Into a 100-mL round-bottom flask was placed (E)-2-(3-ethoxy-3-oxoprop-1-en-1-yl)benzoic acid (4.50 g, 20.43 mmol, 1.00 equiv), EtOH (50.0 mL) and Pd/C (450 mg, 10% Wt). The flask was evacuated and flushed three times with nitrogen, followed by flushing with hydrogen, and then hydrogen pressure was maintained at 20 atm. The mixture was stirred for 12 h at room temperature. The mixture was filtered, and the filtrate was concentrated under reduced pressure. This resulted in 2-(3-ethoxy-3-oxopropyl)benzoic acid, which was used for the next step directly. LCMS (ES, m/z): $[M+H]^+$: 223.

Step 3

Into a 100-mL round-bottom flask was placed 2-(3-ethoxy-3-oxopropyl)benzoic acid (1.00 g, 4.50 mmol, 1.00 equiv), DMF (30 mL), (2S)-piperidin-2-ylmethanol (622 mg, 5.40 mmol, 1.20 equiv), and DIEA (1.16 g, 9.00 mmol, 2.00 equiv). The mixture was cooled to 0° C., and HATU (1.88 g, 4.95 mmol, 1.10 equiv) was added. The resulting solution was warmed up to room temperature and stirred for 1 h. The reaction was quenched with 50 mL of ice water and extracted with 3×100 mL of ethyl acetate. The combined organic phase was washed with 3×100 mL of brine, dried over anhydrous sodium sulfate, and filtered. The filtrate was concentrated under reduced pressure. The residue was purified by silica gel column with ethyl acetate/petroleum ether (1:1) as eluents. This resulted in ethyl (S)-3-(2-(2-(hydroxymethyl)piperidine-1-carbonyl)phenyl)propanoate. LCMS (ES, m/z): $[M+H]^+$: 320.

Step 4

Into a 250-mL 3-necked round-bottom flask purged and maintained with an inert atmosphere of nitrogen was placed ethyl (S)-3-(2-(2-(hydroxymethyl)piperidine-1-carbonyl)phenyl)propanoate (1.00 g, 3.13 mmol, 1.00 equiv), DCM (100 mL), 2,6-dihydroxybenzaldehyde (519 mg, 3.76 mmol, 1.20 equiv), and $PPh_3$ (0.99 g, 3.76 mmol, 1.20 equiv). The solution was cooled to 0° C., and a solution of DBAD (865 mg, 3.76 mmol, 1.20 equiv) in THF (2.0 mL) was added dropwise. The resulting solution was warmed up to room temperature and stirred for 12 h. The mixture was concentrated to remove the solvent, and the residue was purified by silica gel column with ethyl acetate/petroleum ether (1:1) as eluents. This resulted in ethyl 3-[2-[(2S)-2-(2-formyl-3-hydroxyphenoxymethyl)piperidine-1-carbonyl]phenyl]propanoate. LCMS (ES, m/z): $[M+H]^+$: 440.

Step 5

Into a 20-mL round-bottom flask was placed 3-[2-[(2S)-2-(2-formyl-3-hydroxyphenoxymethyl)piperidine-1-carbonyl]phenyl]propanoate (300 mg, 0.68 mmol, 1.00 equiv) and THF (2.0 mL). The solution was cooled to 0° C., and a solution of $LiOH \cdot H_2O$ (86 mg, 2.04 mmol, 3.00 equiv) in $H_2O$ (4.0 mL) was added dropwise. The resulting solution was warmed up to room temperature and stirred for 1 h. The mixture was concentrated to remove the solvent, and the crude product was purified by Prep-HPLC with the following conditions: Column, Atlantis HILIC OBD Column, 19×150 mm, 5 μm, Mobile phase, Water (0.1% FA) and MeCN (40% Phase B up to 60% in 8 min), Detector, UV 254 nm. This resulted in 3-{2-[(2S)-2-[(2-formyl-3-hydroxyphenoxy)methyl]piperidine-1-carbonyl]phenyl}propanoic acid. $^1$H-NMR (300 MHz, DMSO-$d_6$, ppm): δ 12.11 (br, 1H), 11.75 (br, 1H), 10.40-9.85 (m, 1H), 7.56-7.19 (m, 5H), 6.90-6.52 (m, 2H), 5.27-5.15 (m, 1H), 4.56-4.25 (m, 2H), 3.29-3.15 (m, 2H), 2.93-2.51 (m, 3H), 2.46-2.34 (m, 1H), 1.92-1.25 (m, 6H). LCMS (ES, m/z): $[M+H]^+$: 412.2.

Example 9. Synthesis of 3-{2-[(3S)-3-[(2-formyl-3-hydroxyphenoxy)methyl]morpholine-4-carbonyl]phenyl}propanoic acid, Compound 8A Compound 8A was synthesized according to Scheme 9.

Scheme 9

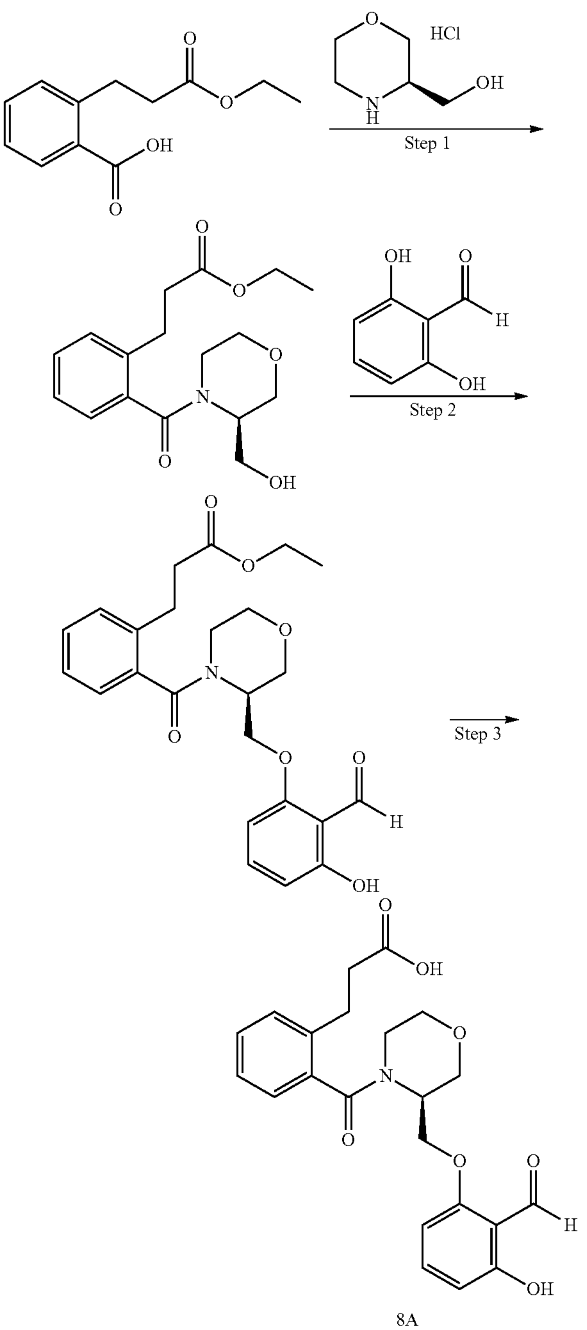

8A

Step 1

Into a 100-mL round-bottom flask was placed 2-(3-ethoxy-3-oxopropyl)benzoic acid (1.00 g, 4.50 mmol, 1.00 equiv), DMF (30 mL), (3R)-morpholin-3-yl-methanol hydrochloride (830 mg, 5.40 mmol, 1.20 equiv), and DIEA (1745 mg, 13.50 mmol, 3.00 equiv). The solution was cooled to 0° C., and HATU (1882 mg, 4.95 mmol, 1.10 equiv) was added. The resulting solution was warmed up to room temperature and stirred for 1 h. The reaction solution was diluted with 30 mL of ice water and extracted with 3×50 mL of ethyl acetate. The combined organic phase was washed with 3×50 mL of brine, dried over anhydrous sodium sulfate, and filtered. The filtrate was concentrated under reduced pressure. The resulting residue was purified by silica gel column with ethyl acetate/petroleum ether (1:1) as eluents. This resulted in ethyl (R)-3-(2-(3-(hydroxymethyl)morpholine-4-carbonyl)phenyl)propanoate. LCMS (ES, m/z): $[M+H]^+$: 322.

Step 2

Into a 100-mL 3-necked round-bottom flask purged and maintained with an inert atmosphere of nitrogen was placed ethyl (R)-3-(2-(3-(hydroxymethyl)morpholine-4-carbonyl)phenyl)propanoate (1.08 g, 3.36 mmol, 1.00 equiv), DCM (50 mL), 2,6-dihydroxybenzaldehyde (557 mg, 4.03 mmol, 1.20 equiv), and $PPh_3$ (1.06 g, 4.03 mmol, 1.20 equiv). The solution was cooled to 0° C., and a solution of DBAD (928 mg, 4.03 mmol, 1.20 equiv) in THF (2.0 mL) was added dropwise. The resulting solution was warmed up to room temperature and stirred for 12 h. The mixture was concentrated to remove the solvent, and the residue was purified by silica gel column with ethyl acetate/petroleum ether (1:1) as eluents. This resulted in ethyl (S)-3-(2-(3-((2-formyl-3-hydroxyphenoxy)methyl)morpholine-4-carbonyl)phenyl)propanoate. LCMS (ES, m/z): $[M+H]^+$: 442.

Step 3

Into a 20-mL vial was placed ethyl (S)-3-(2-(3-((2-formyl-3-hydroxyphenoxy)methyl)morpholine-4-carbonyl)phenyl)propanoate (300 mg, 0.68 mmol, 1.00 equiv) and THF (2.00 mL). The solution was cooled to 0° C., and a solution of $LiOH \cdot H_2O$ (86 mg, 2.04 mmol, 3.00 equiv) in $H_2O$ (4.0 mL) was added dropwise. The resulting solution was warmed up to room temperature and stirred for 1 h. The mixture was concentrated to remove the solvent, and the crude product was purified by Prep-HPLC with the following conditions: Column, Atlantis HILIC OBD Column, 19×150 mm, 5 μm, Mobile phase, Water (0.10% FA) and MeCN (40% Phase B up to 60% in 8 min), Detector, UV 254 nm. This resulted in 3-{2-[(3S)-3-[(2-formyl-3-hydroxyphenoxy)methyl]morpholine-4-carbonyl]phenyl}propanoic acid. $^1$H-NMR (300 MHz, DMSO-$d_6$, ppm): δ 11.77 (br, 2H), 10.41-10.09 (m, 1H), 7.55-6.99 (m, 5H), 6.79-6.50 (m, 2H), 4.98-4.89 (m, 1H), 4.43-3.93 (m, 4H), 3.75-3.42 (m, 4H), 3.12-2.56 (m, 4H). LCMS (ES, m/z): $[M+H]^+$: 414.2.

Example 10. Synthesis of 3-{2-[(3R)-3-[(2-formyl-3-hydroxyphenoxy)methyl]thiomorpholine-4-carbonyl]phenyl}propanoic acid, Compound 9A Compound 9A was synthesized according to Scheme 10.

Scheme 10

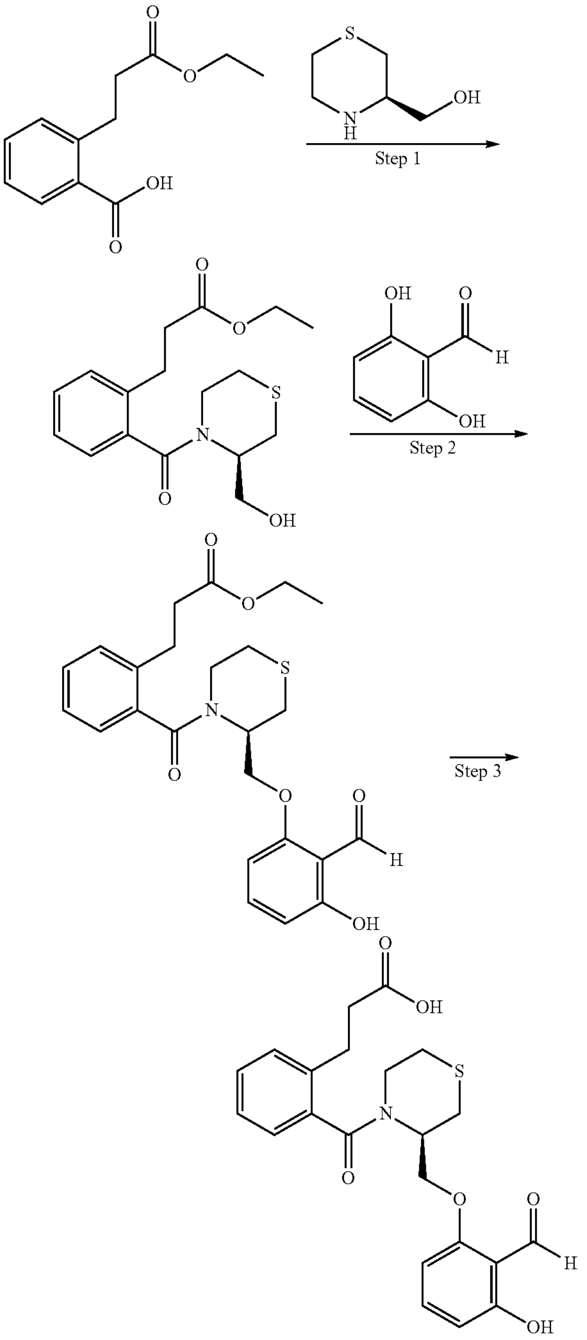

9A

Step 1

Into a 50-mL round-bottom flask was placed 2-(3-ethoxy-3-oxopropyl)benzoic acid (600 mg, 2.70 mmol, 1.00 equiv), DMF (20.00 mL), (3R)-thiomorpholin-3-yl-methanol (432 mg, 3.24 mmol, 1.20 equiv), and DIEA (698 mg, 5.40 mmol, 2.00 equiv). The solution was cooled to 0° C., and HATU (1.23 g, 3.24 mmol, 1.20 equiv) was added. The resulting solution was warmed up to room temperature and stirred for 2 h. The reaction was quenched with 20 mL of ice water and extracted with 3x30 mL of ethyl acetate. The combined organic phase was washed with 3x30 mL of brine, dried over anhydrous sodium sulfate, and filtered. The filtrate was concentrated under reduced pressure. The residue was purified by silica gel column with ethyl acetate/petroleum ether (1:1) as eluents. This resulted in ethyl (R)-3-(2-(3-(hydroxymethyl)thiomorpholine-4-carbonyl)phenyl)propanoate. LCMS (ES) $[M+1]^+$ m/z: 338.

Step 2

Into a 100-mL 3-necked round-bottom flask purged and maintained with an inert atmosphere of nitrogen was placed ethyl (R)-3-(2-(3-(hydroxymethyl)thiomorpholine-4-carbonyl)phenyl)propanoate (700 mg, 2.08 mmol, 1.00 equiv), DCM (30.0 mL), 2,6-dihydroxybenzaldehyde (344 mg, 2.49 mmol, 1.20 equiv), and $PPh_3$ (653 mg, 2.49 mmol, 1.20 equiv). The solution was cooled to 0° C., and a solution of DBAD (573 mg, 2.49 mmol, 1.20 equiv) in THF (2.0 mL) was added dropwise. The resulting solution was warmed up to room temperature and stirred for 12 h. The mixture was concentrated to remove the solvent, and the residue was purified by silica gel column with ethyl acetate/petroleum ether (1:1) as eluents. This resulted in ethyl (R)-3-(2-(3-((2-formyl-3-hydroxyphenoxy)methyl)thiomorpholine-4-carbonyl)phenyl)propanoate. LCMS (ES) [M+1]+m/z: 458.

Step 3

Into a 20-mL vial was placed ethyl 3-[2-[(3R)-3-(2-formyl-3-hydroxyphenoxymethyl)thiomorpholine-4-carbonyl]phenyl]propanoate (300 mg, 0.66 mmol, 1.00 equiv) and THF (2.0 mL). The solution was cooled to 0° C., and a solution of $LiOH \cdot H_2O$ (83 mg, 1.97 mmol, 3.00 equiv) in $H_2O$ (4.0 mL) was added dropwise. The resulting solution was warmed up to room temperature and stirred for 1 h. The mixture was concentrated to remove the solvent, and the crude product was purified by Prep-HPLC with the following conditions: Column, Atlantis HILIC OBD Column, 19x150 mm, 5 μm, Mobile phase, Water (0.1% FA) and MeCN (40% Phase B up to 60% in 8 min), Detector, UV 254 nm. This resulted in 3-{2-[(3R)-3-[(2-formyl-3-hydroxyphenoxy)methyl]thiomorpholine-4-carbonyl]phenyl}propanoic acid. $^1H$-NMR (300 MHz, DMSO-$d_6$, ppm): δ 12.13 (br, 1H), 11.76 (br, 1H), 10.37-10.00 (m, 1H), 7.59-7.20 (m, 5H), 6.78-6.50 (m, 2H), 5.47-5.34 (m, 1H), 4.86-4.43 (m, 2H), 3.48-3.40 (m, 2H), 3.15-3.09 (m, 1H), 2.98-2.51 (m, 6H), 2.47-2.40 (m, 1H). LCMS (ES, m/z): $[M+H]^+$: 430.1.

Example 11. Synthesis of 3-[(2S)-2-[(2-formyl-3-hydroxyphenoxy)methyl]piperidine-1-carbonyl]pyridine-2-carboxylic acid, Compound 1B Compound 1B was synthesized according to Scheme 11.

Scheme 11

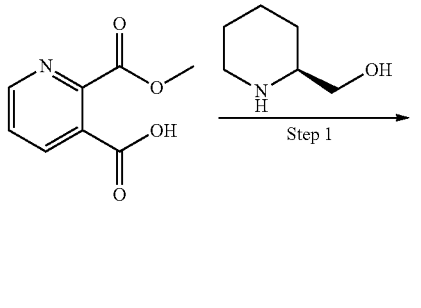

-continued

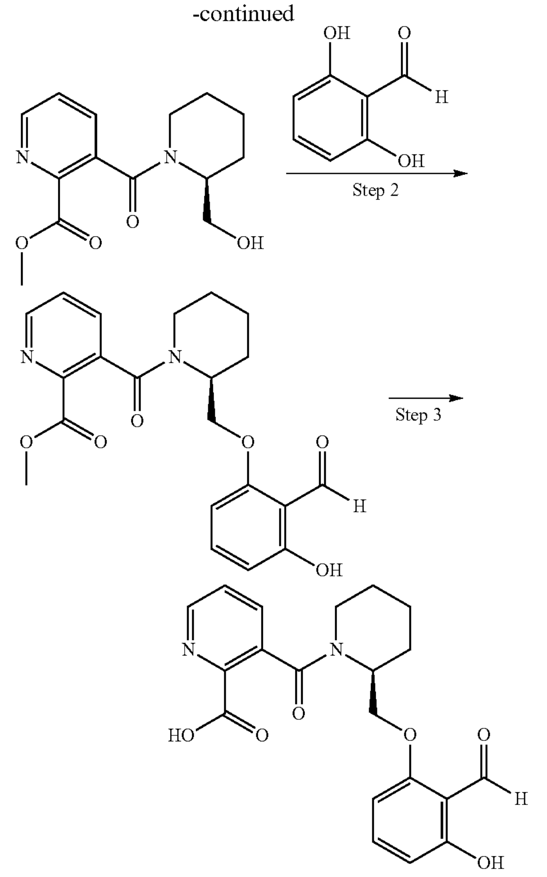

1B

Step 1

Into a 20-mL vial was placed a mixture of 2-(methoxycarbonyl)pyridine-3-carboxylic acid (500 mg, 2.76 mmol, 1.00 equiv), DMF (5.00 mL), (2S)-piperidin-2-ylmethanol (476 mg, 4.14 mmol, 1.50 equiv), DIEA (1.07 g, 8.27 mmol, 3.00 equiv) and HATU (1.57 g, 4.14 mmol, 1.50 equiv). The resulting solution was stirred for 2 hours at room temperature. The crude reaction mixture was filtered and subjected to reverse phase preparative HPLC (Prep-C18, 20-45 mM, 120 g, Tianjin Bonna-Agela Technologies; gradient elution of 10% MeCN in water to 33% MeCN in water over a 15 min period, where both solvents contain 0.1% formic acid). This resulted in methyl 3-[(2S)-2-(hydroxymethyl)piperidine-1-carbonyl]pyridine-2-carboxylate. LCMS (ES) $[M+1]^+$ m/z: 279.2.

Step 2

Into a 40-mL round-bottom flask was placed a mixture of methyl 3-[(2S)-2-(hydroxymethyl)piperidine-1-carbonyl]pyridine-2-carboxylate (500 mg, 1.797 mmol, 1.00 equiv), THF (20.00 mL, 0.277 mmol, 0.15 equiv), 2,6-dihydroxybenzaldehyde (372 mg, 2.69 mmol, 1.50 equiv) and $PPh_3$ (942 mg, 3.59 mmol, 2.00 equiv). DBAD (827 mg, 3.59 mmol, 2.00 equiv) was added dropwise at 0° C. The resulting solution was stirred for 16 hours at room temperature. The resulting mixture was concentrated. The residue was applied onto a silica gel column with ethyl acetate/petroleum ether (2/1~1/1) as eluents. This resulted in methyl 3-[(2S)-2-(2-formyl-3-hydroxyphenoxymethyl)piperidine-1-carbonyl]pyridine-2-carboxylate. LCMS (ES) $[M+1]^+$ m/z: 399.1.

Step 3

Into a 20-mL round-bottom flask was placed a mixture of methyl 3-[(2S)-2-(2-formyl-3-hydroxyphenoxymethyl)piperidine-1-carbonyl]pyridine-2-carboxylate (200 mg, 0.502 mmol, 1.00 equiv), MeOH (5.00 mL), $H_2O$ (1.00 mL) and sodium hydroxide (40.1 mg, 1.00 mmol, 2.00 equiv). The resulting solution was stirred for 1 hour at room temperature. The resulting mixture was concentrated. The crude product was purified by Prep-HPLC with the following conditions: Column, SunFire Prep C18 OBD Column, 19×150 mm, 5 μm; mobile phase, phase A: $H_2O$ (0.1% FA); phase B: MeCN (10% MeCN up to 60% MeCN in 12 min). This resulted in 3-[(2S)-2-[(2-formyl-3-hydroxyphenoxy)methyl]piperidine-1-carbonyl]pyridine-2-carboxylic acid. $^1$H NMR (300 MHz, DMSO-$d_6$, ppm) δ 14.21-12.35 (br, 1H), 11.75 (s, 1H), 10.21 (s, 1H), 8.71-8.66 (m, 1H), 7.84-7.43 (m, 3H), 6.74-6.65 (m, 1H), 6.57-6.50 (m, 1H), 5.21-5.08 (m, 1H), 4.48-4.39 (m, 2H), 3.23-2.94 (m, 2H), 2.08-1.35 (m, 6H). LCMS (ES) [M+1]$^+$ m/z: 385.1.

Example 12. Synthesis of 2-{3-[3-[(2-formyl-3-hydroxyphenoxy)methyl]thiomorpholine-4-carbonyl]pyridin-2-yl}acetic acid (sodium salt), Compound 2B (Enantiomer 1)

Compound 2B, Enantiomer 1 was synthesized according to Scheme 12.

Scheme 12

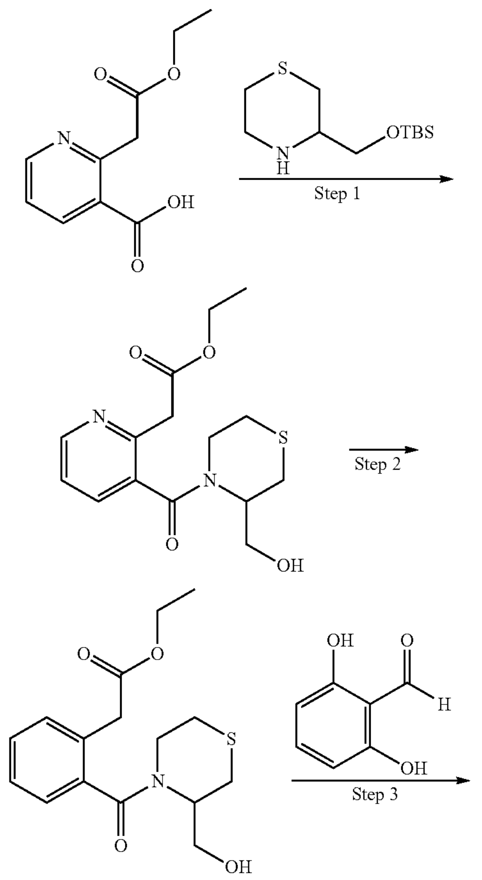

-continued

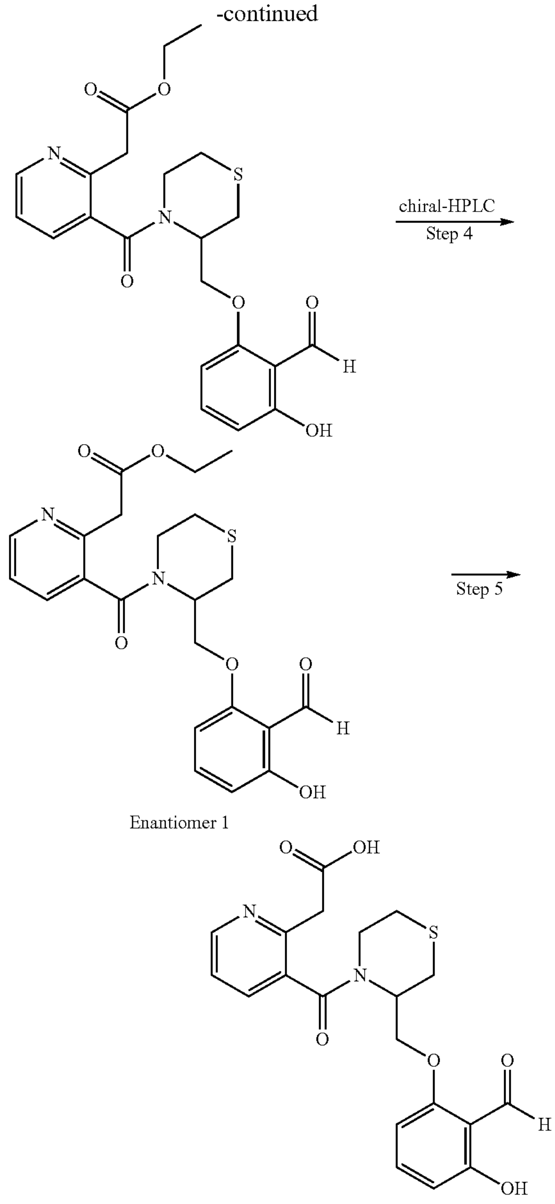

2B
(Enantiomer 1)

Step 1

Into a 100-mL round-bottom flask was placed 2-(2-ethoxy-2-oxoethyl)pyridine-3-carboxylic acid (600.00 mg, 2.868 mmol, 1.00 equiv), DCM (20.00 mL), 3-[[(tert-butyldimethylsilyl)oxy]methyl]thiomorpholine (709.76 mg, 2.868 mmol, 1.00 equiv), HATU (1635.78 mg, 4.302 mmol, 1.50 equiv) and DIEA (1112.03 mg, 8.604 mmol, 3.00 equiv). The resulting solution was stirred for 4 hr at 25° C. The resulting mixture was concentrated, and the residue was applied onto a silica gel column with ethyl acetate/petroleum ether (1:3) as eluents. The collected fractions were combined and concentrated. This resulted in ethyl 2-[3-(3-[[(tert-butyldimethylsilyl)oxy]methyl]thiomorpholine-4-carbonyl)pyridin-2-yl]acetate. LCMS (ES) [M+1]$^+$ m/z: 439.2.

Step 2

Into a 100-mL round-bottom flask was placed ethyl 2-[3-(3-[[(tert-butyldimethylsilyl)oxy]methyl]thiomorpholine-4-carbonyl)pyridin-2-yl]acetate (1.10 g, 2.508 mmol, 1.00 equiv), tetrahydrofuran (20.00 mL), and TBAF (0.13 g, 0.497 mmol, 0.20 equiv). The resulting solution was stirred for 1 hr at 50° C. The resulting mixture was concentrated, and the residue was applied onto a silica gel column with ethyl acetate/petroleum ether (1:2) as eluents. The collected fractions were combined and concentrated. This resulted in ethyl 2-[3-[3-(hydroxymethyl)thiomorpholine-4-carbonyl] pyridin-2-yl]acetate. LCMS (ES) [M+1]+m/z: 325.1.

Step 3

Into a 100-mL round-bottom flask was placed ethyl 2-[3-[3-(hydroxymethyl)thiomorpholine-4-carbonyl]pyridin-2-yl]acetate (600.00 mg, 1.850 mmol, 1.00 equiv), tetrahydrofuran (20 mL), 2,6-dihydroxybenzaldehyde (255 mg, 1.85 mmol, 1.00 equiv), triphenylphosphine (582 mg, 2.219 mmol, 1.20 equiv) and DBAD (511 mg, 2.22 mmol, 1.20 equiv). The resulting solution was stirred for 3 hr at 25° C. The resulting mixture was concentrated, and the residue was applied onto a silica gel column with ethyl acetate/petroleum ether (1:3) as eluents. The collected fractions were combined and concentrated. This resulted in ethyl 2-[3-[3-(2-formyl-3-hydroxyphenoxymethyl)thiomorpholine-4-carbonyl]pyridin-2-yl]acetate. LCMS (ES) [M+1]+m/z: 445.1.

Step 4

The compound ethyl 2-[3-[3-(2-formyl-3-hydroxyphenoxymethyl)thiomorpholine-4-carbonyl]pyridin-2-yl]acetate (380.00 mg, 0.855 mmol, 1.00 equiv) was separated by Chiral Prep-HPLC with the following conditions. Column: CHIRALPAK IC-3, 50×4.6 mm, 3 μm IC30CC-SC002; mobile phase: A: n-Hexane, B: Ethanol; gradient elution of 0% B to 50% B in 35 min. This resulted in ethyl 2-[3-[3-(2-formyl-3-hydroxyphenoxymethyl)thiomorpholine-4-carbonyl]pyridin-2-yl]acetate, Enantiomer 1 (retention time=14.6 min). LCMS (ES) $[M+1]^+$ m/z: 445.1.

Step 5

Into a 50-mL round-bottom flask was placed ethyl 2-[3-[3-(2-formyl-3-hydroxyphenoxymethyl)thiomorpholine-4-carbonyl]pyridin-2-yl]acetate, Enantiomer 1 (100.00 mg, 0.225 mmol, 1.00 equiv), methanol (14.42 mg, 0.450 mmol, 2.00 equiv), water (5 mL) and sodium hydroxide (5 mL). The resulting solution was stirred for 2 hr at 25° C. The resulting mixture was concentrated. The crude reaction mixture was filtered and subjected to reverse phase preparative HPLC (Prep-C18, 20-45M, 120 g, Tianjin Bonna-Agela Technologies; gradient elution of 20% MeCN in water to 30% MeCN in water over a 10 min period, where both solvents contain 0.1% $NH_4HCO_3$) to provide Compound 2B, Enantiomer 1. $^1H$ NMR (300 MHz, DMSO-$d_6$, ppm) δ 10.33-9.86 (m, 1H), 8.45-8.36 (m, 1H), 7.81-7.00 (m, 3H), 6.31-5.95 (m, 2H), 5.41-5.05 (m, 1H), 4.91-4.10 (m, 3H), 3.90-3.54 (m, 3H), 3.24-3.15 (m, 2H), 2.95-2.86 (m, 1H), 2.35-2.18 (m, 1H). LCMS (ES) $[M+1]^+$ m/z: 417.0.

Example 13. Synthesis of 3-[(3S)-3-[(2-formyl-3-hydroxyphenoxy)methyl]morpholine-4-carbonyl] pyridine-2-carboxylic acid, Compound 3B Compound 3B was synthesized according to Scheme 13.

Scheme 13

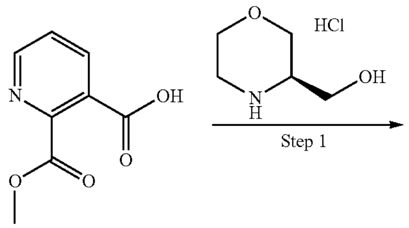

-continued

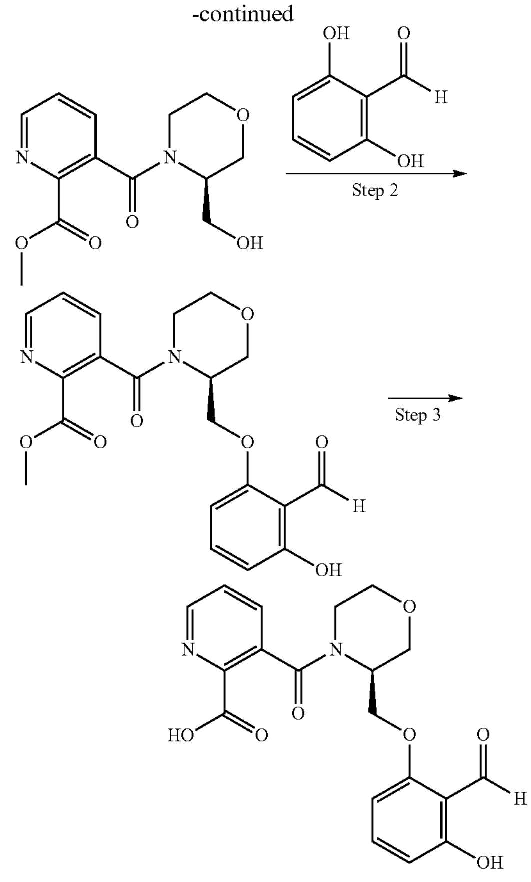

3B

Step 1

Into a 50-mL 3-necked round-bottom flask was placed 2-(methoxycarbonyl)pyridine-3-carboxylic acid (1.0 g, 5.52 mmol, 1.0 equiv), DMF (10 mL), (3R)-morpholin-3-ylmethanol hydrochloride (1.02 g, 6.62 mmol, 1.2 equiv) and DIEA (0.86 g, 6.62 mmol, 1.2 equiv). This was followed by the addition of HATU (2.52 g, 6.62 mmol, 1.2 equiv) in three batches at 0° C. The mixture was stirred overnight at room temperature. The reaction solution was then directly purified by Flash-Prep-HPLC with conditions: C18-120 g column, MeCN/$H_2O$ (0.05% $NH_4OH$), from 5% to 70% in 12 min, flow rate: 70 mL/min, detector: 254 nm. This resulted in methyl 3-[(3R)-3-(hydroxymethyl)morpholine-4-carbonyl] pyridine-2-carboxylate. LCMS (ES) $[M+1]^+$ m/z: 281.

Step 2

Into a 100-mL 3-necked round-bottom flask purged and maintained with an inert atmosphere of nitrogen was placed methyl 3-[(3R)-3-(hydroxymethyl)morpholine-4-carbonyl] pyridine-2-carboxylate (787 mg, 2.81 mmol, 1.0 equiv), THF (50 mL), 2,6-dihydroxybenzaldehyde (465 mg, 3.37 mmol, 1.2 equiv) and $PPh_3$ (884 mg, 3.37 mmol, 1.2 equiv). A solution of DBAD (776 mg, 3.37 mmol, 1.2 equiv) in THF (2 mL) was added dropwise with stirring at 0° C. The mixture was warmed to room temperature and stirred overnight. The mixture was concentrated to remove the solvent, and the residue was purified by silica gel column with ethyl acetate/petroleum ether as eluents (80%). This resulted in methyl 3-[(3S)-3-(2-formyl-3-hydroxyphenoxymethyl)morpholine-4-carbonyl]pyridine-2-carboxylate. LCMS (ES) $[M+1]^+$ m/z: 401.

Step 3

Into a 50-mL round-bottom flask was placed methyl 3-[(3S)-3-(2-formyl-3-hydroxyphenoxymethyl)morpholine-4-carbonyl]pyridine-2-carboxylate (300 mg, 0.75 mmol, 1.0 equiv) and THF (5 mL). A solution of $LiOH{\cdot}H_2O$ (95 mg, 2.25 mmol, 3.0 equiv) in $H_2O$ (10 mL) was added dropwise with stirring at 0° C. The reaction solution was warmed up to room temperature and stirred for 2 h. The solution was adjusted to pH=6 with HCl (3M) and extracted with 3×20 mL of dichloromethane. The combined organic phase was concentrated under reduced pressure. The crude product was purified by Flash-Prep-HPLC with the following conditions (IntelFlash-1): Column: Ascentis Express C18, 50×3.0 mm, 2.7 μm, Mobile Phase A: Water/0.05% FA, Mobile Phase B: MeCN, Flow rate: 1.5 mL/min, Gradient: 5% B to 100% B in 1.2 min, hold 0.6 min. This resulted in 3-[(3S)-3-(2-formyl-3-hydroxyphenoxymethyl)morpholine-4-carbonyl] pyridine-2-carboxylic acid. $^1$H NMR (300 MHz, DMSO-$d_6$, ppm): δ 13.50 (br, 1H), 11.79 (s, 1H), 10.30 (s, 1H), 8.74-8.71 (m, 1H), 7.91-7.80 (m, 1H), 7.71-7.42 (m, 2H), 6.74 (d, J=8.1 Hz, 1H), 6.57-6.51 (m, 1H), 4.83-4.80 (m, 1H), 4.47-4.11 (m, 3H), 3.94-3.04 (m, 5H). LCMS (ES, m/z): $[M+H]^+$: 387.1.

Example 14. Synthesis of 2-{3-[(3S)-3-[(2-formyl-3-hydroxyphenoxy)methyl]morpholine-4-carbonyl] pyridin-2-yl}acetic acid (sodium salt), Compound 4B Compound 4B was synthesized according to Scheme 14.

Scheme 12

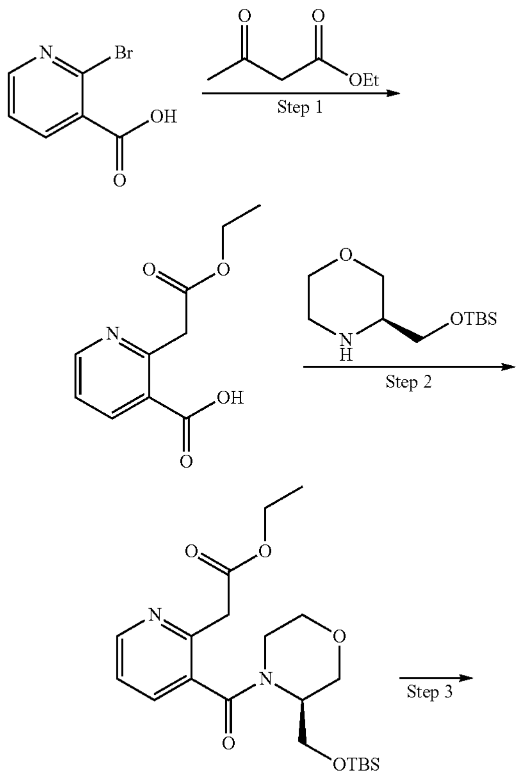

-continued

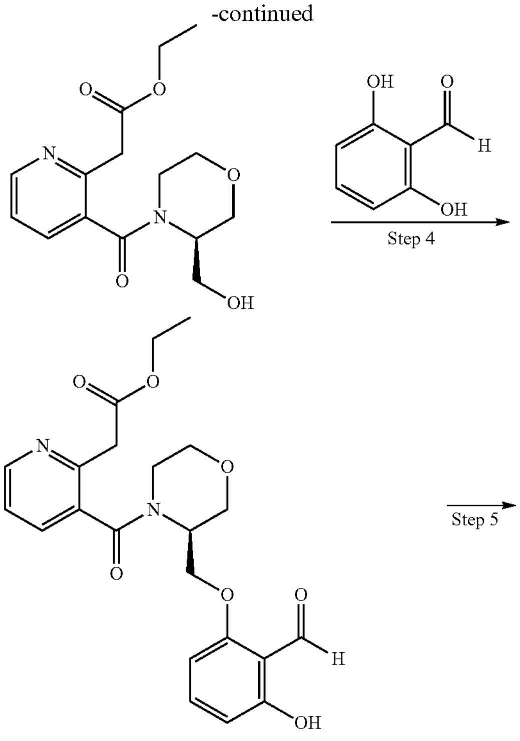

Enantiomer 1

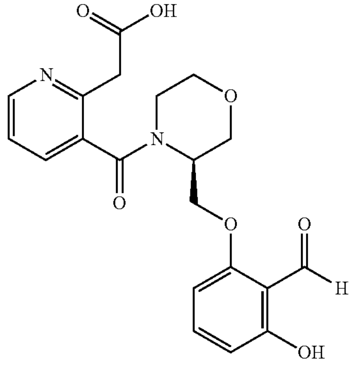

4B

Step 1

Into a 100-mL round-bottom flask was placed 2-bromopyridine-3-carboxylic acid (2.00 g, 9.901 mmol, 1.00 equiv), ethyl acetoacetate (1.93 g, 14.852 mmol, 1.50 equiv), sodium ethoxide (2.94 g, 14.851 mmol, 1.50 equiv), $Cu(OAc)_2$ (1.80 g, 9.901 mmol, 1.0 equiv) and EtOH (30 mL). The resulting solution was stirred for 16 hr at 80° C. The resulting mixture was concentrated under vacuum, and the residual solution was extracted with 3×30 mL of ethyl acetate. The organic layers were combined, dried over anhydrous sodium sulfate, and concentrated. The residue was applied onto a silica gel column with chloroform/methanol (10:1) as eluents. This resulted in 2-(2-ethoxy-2-oxoethyl)pyridine-3-carboxylic acid. LCMS (ES) $[M+1]^+$ m/z: 210.1.

Step 2

Into a 100-mL round-bottom flask was placed 2-(2-ethoxy-2-oxoethyl)pyridine-3-carboxylic acid (1.10 g, 5.258 mmol, 1.00 equiv), (3S)-3-[[(tert-butyldimethylsilyl)oxy] methyl]morpholine (1.83 g, 7.887 mmol, 1.5 equiv), HATU (3.00 g, 7.887 mmol, 1.5 equiv), DIEA (2.04 g, 15.774 mmol, 3 equiv) and DMF (30.00 mL). The resulting solution was stirred for 16 hr at room temperature. The resulting solution was extracted with 3×30 mL of ethyl acetate, and the organic layers were combined, dried over anhydrous sodium sulfate, and concentrated under vacuum. The residue was applied onto a silica gel column with ethyl acetate/petroleum ether (1:2) as eluents. This resulted in ethyl 2-[3-[(3S)-3-[[(tert-butyldimethylsilyl)oxy]methyl]morpholine-4-carbonyl]pyridin-2-yl]acetate. LCMS (ES) $[M+1]^+$ m/z: 423.2.

Step 3

Into a 100-mL 3-necked round-bottom flask purged and maintained with an inert atmosphere of nitrogen was placed ethyl 2-[3-[(3S)-3-[[(tert-butyldimethylsilyl)oxy]methyl] morpholine-4-carbonyl]pyridin-2-yl]acetate (800.00 mg, 1.893 mmol, 1.00 equiv), TBAF (1979.85 mg, 7.572 mmol, 4.00 equiv) and THF (15.00 mL).

The resulting solution was stirred for 16 hr at room temperature. The resulting solution was extracted with 3×30 mL of ethyl acetate, and the organic layers were combined, dried over anhydrous sodium sulfate, and concentrated under vacuum. The residue was applied onto a silica gel column with THF:PE (1:2) as eluents. This resulted in ethyl 2-[3-[(3R)-3-(hydroxymethyl)morpholine-4-carbonyl]pyridin-2-yl]acetate. LCMS (ES) $[M+1]^+$ m/z: 309.1.

Step 4

Into a 100-mL 3-necked round-bottom flask purged and maintained with an inert atmosphere of nitrogen was placed ethyl 2-[3-[(3R)-3-(hydroxymethyl)morpholine-4-carbonyl] pyridin-2-yl]acetate (0.50 g, 1.622 mmol, 1.00 equiv), 2,6-dihydroxybenzaldehyde (0.33 g, 2.416 mmol, 1.49 equiv), DIAD (0.49 g, 2.432 mmol, 1.5 equiv), triphenylphosphine (0.64 g, 2.440 mmol, 1.50 equiv) and THF (30.00 mL). The resulting solution was stirred for 16 hr at room temperature. The resulting solution was extracted with 3×30 mL of ethyl acetate, and the organic layers were combined, dried over anhydrous sodium sulfate, and concentrated under vacuum. The residue was applied onto a silica gel column with THF:PE (1:2) as eluents. This resulted in ethyl 2-[3-[(3S)-3-(2-formyl-3-hydroxyphenoxymethyl)morpholine-4-carbonyl]pyridin-2-yl]acetate. LCMS (ES) $[M+1]^+$ m/z: 429.2.

Step 5

Into a 50-mL round-bottom flask was placed ethyl 2-[3-[(3S)-3-(2-formyl-3-hydroxyphenoxymethyl)morpholine-4-carbonyl]pyridin-2-yl]acetate (300.00 mg, 0.700 mmol, 1.00 equiv), sodium hydroxide (33.61 mg, 0.840 mmol, 1.20 equiv), tetrahydrofuran (10.00 mL), and water (2.00 mL). The resulting solution was stirred for 2 hr at room temperature. The solids were filtered out. The crude product was purified by Prep-HPLC with the following conditions (2 #SHIMADZU (HPLC-01)): Column: Welch XB-C18, 21.2×250 mm, 5 μm; mobile phase: MeCN and Water (0.05% $NH_3H_2O$) (5% Phase B to 35% in 15 min). This resulted in 2-{3-[(3S)-3-[(2-formyl-3-hydroxyphenoxy)methyl]morpholine-4-carbonyl]pyridin-2-yl}acetic acid (sodium salt). $^1H$ NMR (300 MHz, DMSO-$d_6$, ppm) δ 10.10-9.83 (m, 1H), 8.60-8.31 (m, 1H), 7.74-6.76 (m, 3H), 6.02-5.46 (m, 2H), 4.90-4.58 (m, 1H), 4.36-3.40 (m, 8H), 3.18-3.09 (m, 2H). LCMS (ES) $[M+1]^+$ m/z: 401.0.

Example 15. Synthesis of (S)-2-(3-(2-((2-formyl-3-hydroxyphenoxy)methyl)piperidine-1-carbonyl)pyridin-2-yl)acetic acid (sodium salt), Compound 5B Compound 5B was synthesized according to Scheme 15.

Scheme 15

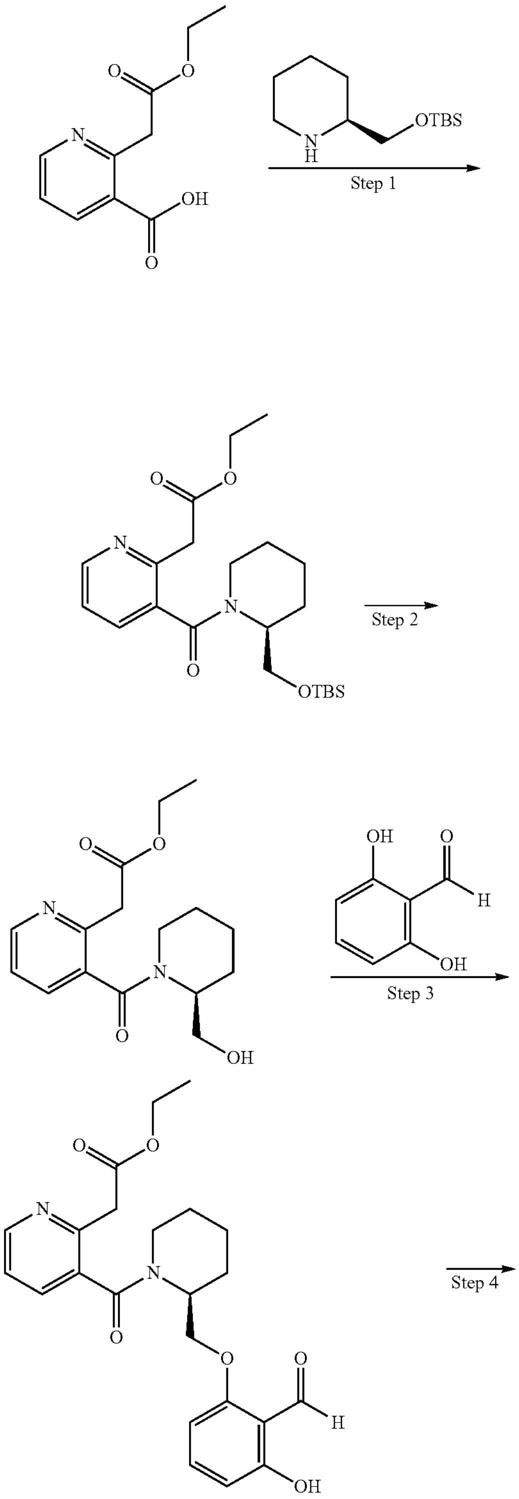

-continued

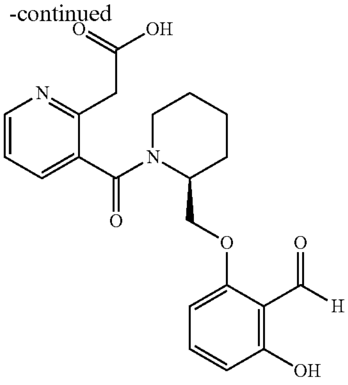

5B

Step 1

Into a 100-mL round-bottom flask was placed 2-(2-ethoxy-2-oxoethyl)pyridine-3-carboxylic acid (1.00 g, 4.780 mmol, 1.00 equiv), (2S)-2-[[(tert-butyldimethylsilyl)oxy]methyl]piperidine (1.32 g, 5.753 mmol, 1.20 equiv), HATU (2.73 g, 7.170 mmol, 1.5 equiv), DIEA (1.85 g, 14.340 mmol, 3 equiv) and DCM (20.00 mL). The resulting solution was stirred for 6 hr at room temperature. The resulting solution was extracted with 3×50 mL of dichloromethane. The organic layers were combined, dried over anhydrous sodium sulfate, and concentrated under vacuum. The residue was applied onto a silica gel column with ethyl acetate/petroleum ether (1:3) as eluents. This resulted in ethyl 2-[3-[(2S)-2-[[(tert-butyldimethylsilyl)oxy]methyl]piperidine-1-carbonyl]pyridin-2-yl]acetate. LCMS (ES) $[M+1]^+$ m/z: 421.2.

Step 2

Into a 100-mL round-bottom flask was placed ethyl 2-[3-[(2S)-2-[[(tert-butyldimethylsilyl)oxy]methyl]piperidine-1-carbonyl]pyridin-2-yl]acetate (800.00 mg, 1.902 mmol, 1.00 equiv), TBAF (1.99 g, 7.608 mmol, 4.00 equiv) and tetrahydrofuran (20.00 mL). The resulting solution was stirred for 4 hr at room temperature. The resulting solution was extracted with 3×20 mL of ethyl acetate. The organic layers were combined, dried over anhydrous sodium sulfate, and concentrated under vacuum. The residue was applied onto a silica gel column with ethyl acetate/petroleum ether (1:1.5) as eluents. This resulted in ethyl 2-[3-[(2S)-2-(hydroxymethyl)piperidine-1-carbonyl]pyridin-2-yl]acetate. LCMS (ES) [M+1]+m/z: 307.1.

Step 3

Into a 100-mL 3-necked round-bottom flask purged and maintained with an inert atmosphere of nitrogen was placed ethyl 2-[3-[(2S)-2-(hydroxymethyl)piperidine-1-carbonyl]pyridin-2-yl]acetate (550.00 mg, 1.795 mmol, 1.00 equiv), 2,6-dihydroxybenzaldehyde (297.56 mg, 2.154 mmol, 1.20 equiv), $PPh_3$ (706.31 mg, 2.693 mmol, 1.5 equiv), THF (15.00 mL) and DIAD (544.52 mg, 2.693 mmol, 1.50 equiv). The resulting solution was stirred for 16 hr at room temperature. The resulting solution was extracted with 3×30 mL of ethyl acetate. The organic layers were combined, dried over anhydrous sodium sulfate, and concentrated under vacuum. The residue was applied onto a silica gel column with THF/PE (1:2) as eluents. This resulted in ethyl 2-[3-[(2S)-2-(2-formyl-3-hydroxyphenoxymethyl)piperidine-1-carbonyl]pyridin-2-yl]acetate. LCMS (ES) [M+1]+ m/z: 427.1.

Step 4

Into a 50-mL round-bottom flask was placed ethyl 2-[3-[(2S)-2-(2-formyl-3-hydroxyphenoxymethyl)piperidine-1-carbonyl]pyridin-2-yl]acetate (260.00 mg, 0.610 mmol, 1.00 equiv), NaOH (97.56 mg, 2.439 mmol, 4.00 equiv), THF (10.00 mL) and $H_2O$ (2.00 mL). The resulting solution was stirred for 4 hr at room temperature and was subsequently concentrated under vacuum. The residue was dissolved in 5 mL of $H_2O$. The crude product was purified by Prep-HPLC with the following conditions (2 #SHIMADZU (HPLC-01)): Column, Atlantis HILIC OBD Column, 19×150 mm, 5 μm; mobile phase: Water (10 mmol/L $NH_4HCO_3$) and MeCN (10% Phase B up to 30% in 8 min). This resulted in (S)-2-(3-(2-((2-formyl-3-hydroxyphenoxy)methyl)piperidine-1-carbonyl)pyridin-2-yl)acetic acid (sodium salt). $^1H$ NMR (300 MHz, DMSO-$d_6$, ppm) δ 11.77 (br, 1H), 10.41-10.05 (m, 1H), 8.59-8.32 (m, 1H), 7.86-6.17 (m, 5H), 5.42-4.81 (m, 1H), 4.61-3.93 (m, 3H), 3.88-3.48 (m, 2H), 3.32-3.25 (m, 1H), 2.01-1.25 (m, 6H). LCMS (ES) $[M+1]^+$ m/z: 399.1.

Example 16. Synthesis of 3-[3-[(2-formyl-3-hydroxyphenoxy)methyl]thiomorpholine-4-carbonyl]pyridine-2-carboxylic acid, Compound 6B (Enantiomer 1)

Compound 6B, Enantiomer 1 was synthesized according to Scheme 16.

Scheme 16

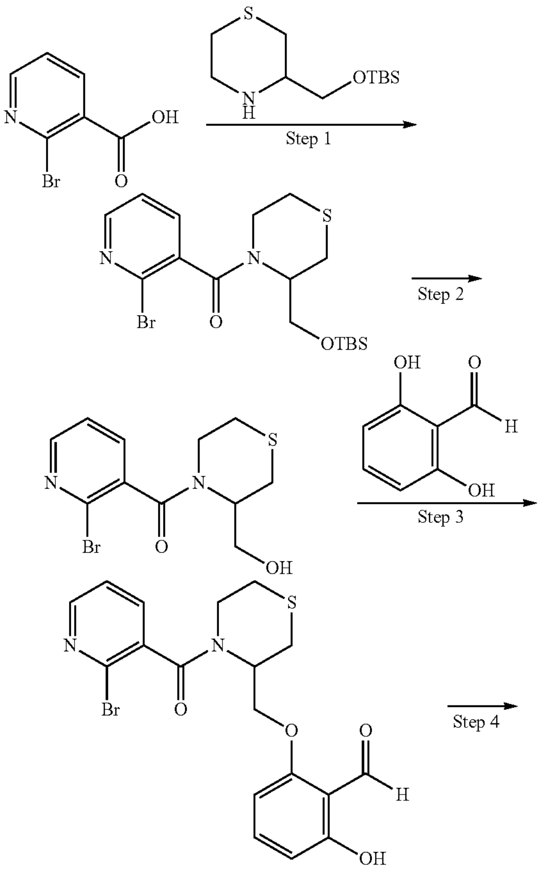

-continued

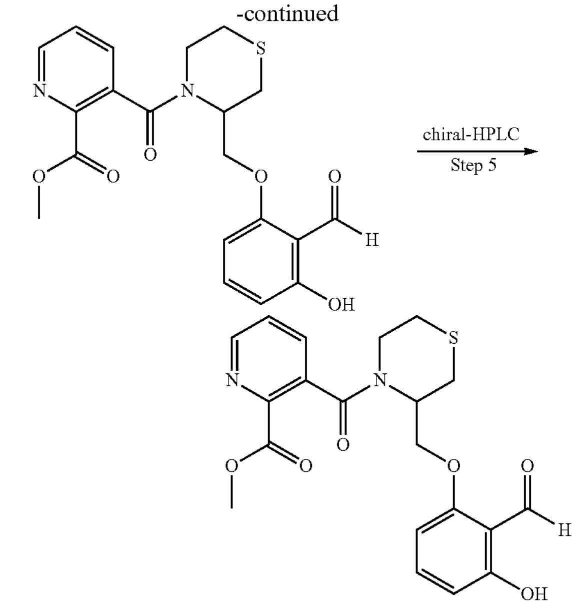

Enantiomer 1

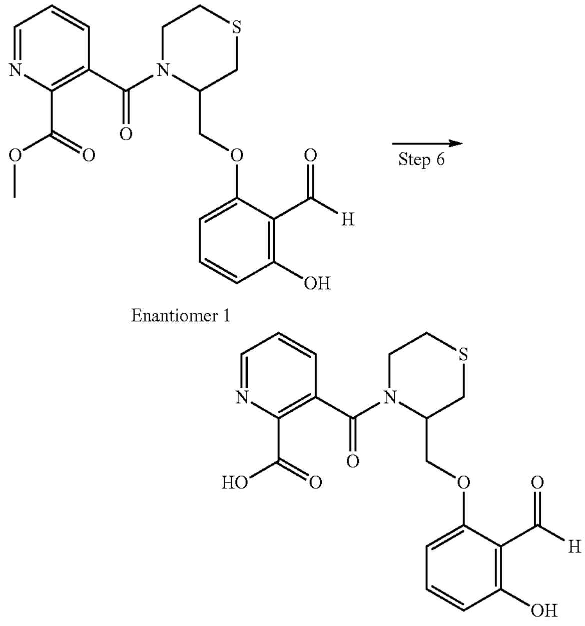

Enantiomer 1

6B
(Enantiomer 1)

Step 1

Into a 100-mL 3-necked round-bottom flask was placed 2-bromopyridine-3-carboxylic acid (1.50 g, 7.43 mmol, 1.0 equiv), DMF (20 mL), 3-[[(tert-butyldimethylsilyl)oxy] methyl]thiomorpholine (2.02 g, 8.17 mmol, 1.1 equiv) and DIEA (1.92 g, 14.85 mmol, 2.0 equiv). This was followed by the addition of HATU (4.24 g, 11.14 mmol, 1.5 equiv) in four batches at 0° C. The mixture was warmed up to room temperature and stirred for 2 h. The reaction was diluted with 10 mL of water and extracted with 3×20 mL of ethyl acetate. The combined organic phase was washed with 3×20 mL of brine, dried over anhydrous sodium sulfate, and filtered. The filtrate was concentrated under reduced pressure. The residue was purified by silica gel column with ethyl acetate/petroleum ether (1:3) as eluents. This resulted in 4-(2-bromopyridine-3-carbonyl)-3-[[(tert-butyldimethylsilyl)oxy]methyl]thiomorpholine. LCMS (ES) $[M+1]^+$ m/z: 431.

Step 2

Into a 100-mL round-bottom flask was placed 4-(2-bromopyridine-3-carbonyl)-3-[[(tert-butyldimethylsilyl)oxy] methyl]thiomorpholine (3.0 g, 6.95 mmol, 1.0 equiv), THF (40 mL) and TEA·3HF (11.21 g, 69.53 mmol, 10.0 equiv). The reaction solution was stirred overnight at room temperature. The reaction solution was directly purified by Prep-HPLC with conditions: C18-120 g column, MeCN/$H_2O$ (0.1% $NH_4OH$), from 5% to 100% within 12 min, flow rate: 70 mL/min, detector: 254 nm. This resulted in [4-(2-bromopyridine-3-carbonyl)thiomorpholin-3-yl]methanol. LCMS (ES) $[M+1]^+$ m/z: 317.

Step 3

Into a 100-mL 3-necked round-bottom flask purged and maintained with an inert atmosphere of nitrogen was placed [4-(2-bromopyridine-3-carbonyl)thiomorpholin-3-yl] methanol (1.20 g, 3.78 mmol, 1.0 equiv), THF (20 mL), 2,6-dihydroxybenzaldehyde (627 mg, 4.54 mmol, 1.2 equiv) and $PPh_3$ (1.19 g, 4.54 mmol, 1.2 equiv). This was followed by the addition of a solution of DBAD (1.05 g, 4.54 mmol, 1.2 equiv) in THF (2 mL) dropwise with stirring at 0° C. The resulting solution was warmed up to room temperature and stirred overnight. The solution was concentrated to remove the solvent, and the residue was purified by silica gel column with EA/PE (1:2) as eluents. This resulted in 2-[[4-(2-bromopyridine-3-carbonyl)thiomorpholin-3-yl]methoxy]-6-hydroxybenzaldehyde. LCMS (ES) $[M+1]^+$ m/z: 437.

Step 4

Into a 100-mL pressure tank reactor was placed 2-[[4-(2-bromopyridine-3-carbonyl)thiomorpholin-3-yl]methoxy]-6-hydroxybenzaldehyde (600 mg, 1.37 mmol, 1.0 equiv), MeOH (20 mL), $Pd(dppf)Cl_2 \cdot CH_2Cl_2$ (56 mg, 0.07 mmol, 0.05 equiv), TEA (556 mg, 5.49 mmol, 4.0 equiv) and CO (excess, and the pressure was maintained at 20 atm). The mixture was stirred overnight at 80° C. in an oil bath. The solution was concentrated to remove the solvent, and the residue was purified by silica gel column with ethyl acetate/petroleum ether (1:2) as eluents. This resulted in methyl 3-[3-(2-formyl-3-hydroxyphenoxymethyl)thiomorpholine-4-carbonyl]pyridine-2-carboxylate. LCMS (ES) $[M+1]^+$ m/z: 417.

Step 5

Methyl 3-[3-(2-formyl-3-hydroxyphenoxymethyl)thiomorpholine-4-carbonyl]pyridine-2-carboxylate was purified by Chiral-Prep-HPLC with conditions: Column: CHIRALPAK IA-3, 20*250 mm, 5 um, Mobile phase: A: n-Hexane B: Ethanol, Flow rate: 17 mL/min, Gradient: 50% B in 35 min, detector: 220 nm. This resulted in methyl 3-[3-(2-formyl-3-hydroxyphenoxymethyl)thiomorpholine-4-carbonyl]pyridine-2-carboxylate, Enantiomer 1 (retention time=25 min, LCMS (ES) $[M+1]^+$ m/z: 417) and methyl 3-[3-(2-formyl-3-hydroxyphenoxymethyl)thiomorpholine-4-carbonyl]pyridine-2-carboxylate, Enantiomer 2 (retention time=20 min, LCMS (ES) $[M+1]^+$ m/z: 417).

Step 6

Into a 8-mL vial was placed methyl 3-[3-(2-formyl-3-hydroxyphenoxymethyl)thiomorpholine-4-carbonyl]pyridine-2-carboxylate, Enantiomer 1 (110 mg, 0.26 mmol, 1.0 equiv) and THF (1.0 mL). This was followed by the addition of a solution of $LiOH{\cdot}H_2O$ (33 mg, 0.79 mmol, 3.0 equiv) in $H_2O$ (2 mL) dropwise with stirring at 0° C. The mixture was warmed up to room temperature and stirred for 2 h. The solution was adjusted to pH=5-6 with HCl (3M) and extracted with DCM (3×20 mL). The combined organic phase was concentrated, and the crude product was purified by Flash-Prep-HPLC with the following conditions (Intel-Flash-1): Column: Ascentis Express C18, 50×3.0 mm, 2.7 μm, Mobile Phase A: Water/0.05% FA, Mobile Phase B: MeCN, Flow rate: 1.5 mL/min, Gradient: 5% B to 100% B in 1.2 min, hold 0.6 min. This resulted in Compound 6B, Enantiomer 1. $^1$H NMR (300 MHz, DMSO-$d_6$, ppm): δ 11.81 (s, 1H), 10.30 (s, 1H), 8.74-8.69 (m, 1H), 7.70-7.44 (m, 3H), 6.74-6.52 (m, 2H), 5.30-4.47 (m, 3H), 3.20-2.98 (m, 5H), 2.49-2.37 (m, 1H). LCMS (ES, m/z) $[M+H]^+$: 403.2. Chiral-HPLC: retention time=4.55 min. Chiral HPLC Instrument: SHIMADZU LC-20AD; Mobile Phase A: MTBE (0.2% MSA); Mobile Phase B: Ethanol/MeOH=1:1; Conc. of Phase B: 10.0%; Flow Rate: 1.000 mL/min Column: CHIRALPAK IA-3, 50×4.6 mm, 3 μm, IA30CC-UL005.

Biological Assays

Whole Blood Assay:

Oxygen equilibrium curves (OECs) were collected using a TCS Hemox Analyzer (TCS Scientific Company, New Hope, PA, USA) to measure changes in the binding affinity of $O_2$ to Hb. Whole blood was incubated for 1 h at 37° C. with the indicated compounds in an equimolar ratio of hemoglobin to compound and diluted into TES (2-[[1,3-dihydroxy-2-(hydroxymethyl)propan-2-yl]amino]ethanesulfonic acid)/saline buffer prior to measurements. The diluted samples were then oxygenated with compressed air within the Hemox Analyzer and the OECs were collected during deoxygenation as previously described (Guarnone et al., *Haematologica,* 1995, 80, 426-430). p 50 (partial pressure of 02 at which Hb is 50% saturated with 02) values were obtained using a non-linear regression analysis. Percentage change in p 50 [Δp50(%)]was calculated as follows: Δp50 (%)=[(p 50 of control)-p 50 with compound)/p 50 control]x 100. The sodium salts of compounds 2B (Enantiomer 1), 4B, and 5B described above were used. Resulting data is shown in Table 3.

TABLE 3

| Compound Number | Delta-p50 (%) |
|---|---|
| 1A | 66.43 |
| 2A | 4.19 |
| 3A | 11.72 |
| 4A | 63.6 |
| 5A (Enantiomer 1) | 11.04 |
| 5A (Enantiomer 2) | 19.57 |
| 6A | 5.09 |
| 7A | 77.13 |
| 8A | 55.01 |
| 9A | 46.78 |
| 1B | 0.4 |
| 2B (Enantiomer 1) | 10.72 |
| 3B | 0.65 |
| 4B | −8.28 |
| 5B | −3.32 |
| 6B (Enantiomer 1) | 14.15 |

Structures of reference compounds (Compound A and Compound B) are shown below in Table 4.

TABLE 4

| | Reference Compound A | Reference Compound B |
|---|---|---|
| Structure | 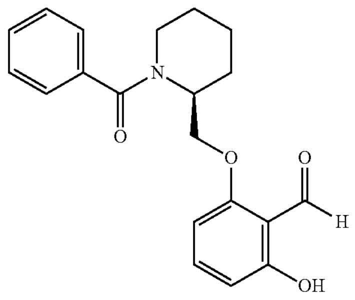 [SMILES: O=Cc1c(O)cccc1OC[C@@H]1CCCCN1C(=O)c1ccccc1] | 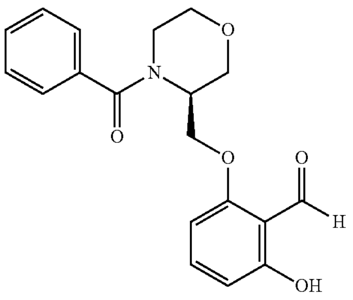 [SMILES: O=Cc1c(O)cccc1OC[C@@H]1COCCN1C(=O)c1ccccc1] |

Rat PK:

A group of fasted male Sprague-Dawley rats were dosed via oral gavage at 2 mg/kg and/or 10 mg/kg with test articles formulated in 0.5% methylcellulose suspension with 0.01% polysorbate 80 in PBS (phosphate buffered saline). Blood samples were collected through jugular vein at pre-selected time points. Blood samples were prepared by protein precipitation with ACN, vortexed and then centrifuged before supernatants were transferred for bioanalysis. Test article concentrations were measured by HPLC-MS-MS. Pharmacokinetic parameters were calculated using non-compartment analysis. The $T_{1/2}$ was calculated via a linear regression of the terminal phase of the blood-time concentration profile.

Results for various compounds disclosed herein (sodium salt of compound 5B described above was used) and select reference compounds (Compound A and Compound B) are summarized in Table 5A and Table 5B.

TABLE 5A

| Compound | $T_{1/2}$ (h) |
|---|---|
| Reference Compound A | 25.9 |
| Reference Compound B | 29.8 |
| 1A | 110 |
| 5A (Enantiomer 1) | 213 |
| 5A (Enantiomer 2) | 13 |
| 4A | 89.2 |
| 7A | 52 |
| 8A | 102 |
| 9A | 88.7 |

TABLE 5B

| Compound Number | $T_{1/2}$ (h) |
|---|---|
| 1B | 11.73 |
| 5B | 120 |

Unless otherwise defined, all technical and scientific terms used herein have the same meaning as commonly understood by one of ordinary skill in the art.

The disclosure illustratively described herein may suitably be practiced in the absence of any element or elements, limitation or limitations, not specifically disclosed herein. Thus, for example, the terms “comprising”, “including,” “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula I:

I

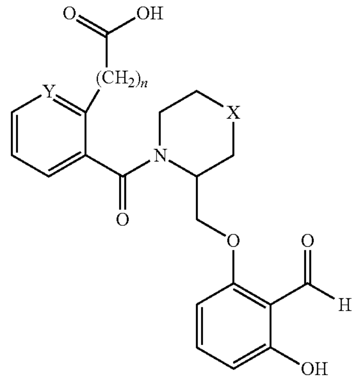

or an isotopically enriched analog, stereoisomer, mixture of stereoisomers, or prodrug thereof, or a pharmaceutically acceptable salt of each thereof, wherein:

Y is CH or N;

X is $CH_2$, O, or S; and n is 0, 1, or 2.

2. The compound of claim 1, wherein the compound is a compound of formula II:

II

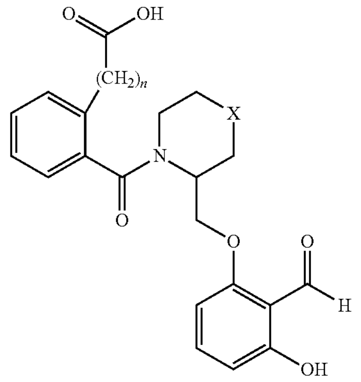

or an isotopically enriched analog, stereoisomer, mixture of stereoisomers, or prodrug thereof, or a pharmaceutically acceptable salt of each thereof, wherein:

X is $CH_2$, O, or S; and n is 0, 1, or 2.

3. The compound of claim 2, wherein the compound is a compound of formula II(a):

II(a)

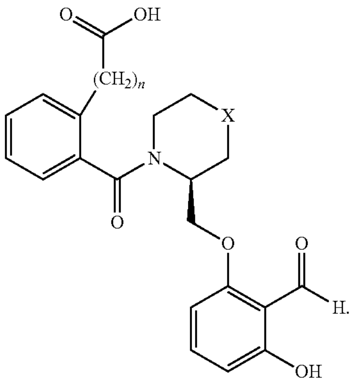

4. The compound of claim 2, wherein the compound is a compound of formula II(b):

II(b)

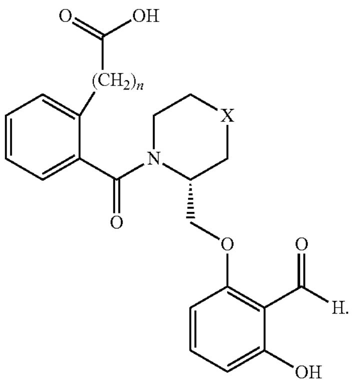

5. The compound of claim 1, wherein the compound is a compound of formula III:

III

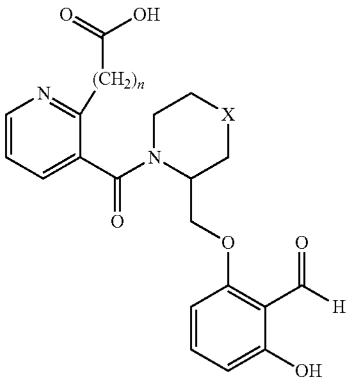

or an isotopically enriched analog, stereoisomer, mixture of stereoisomers, or prodrug thereof, or a pharmaceutically acceptable salt of each thereof, wherein:

X is $CH_2$, O, or S; and n is 0, 1, or 2.

6. The compound of claim 5, wherein the compound is a compound of formula III(a):

III(a)

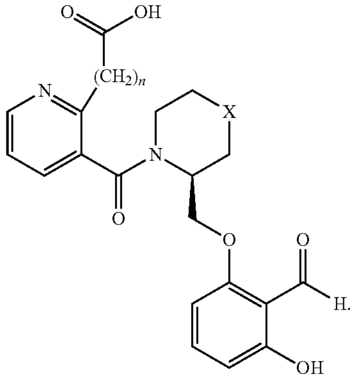

7. The compound of claim 5, wherein the compound is a compound of formula III(b):

III(b)

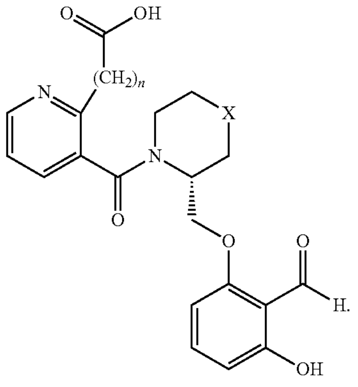

8. The compound of claim 1, wherein X is $CH_2$.

9. The compound of claim 1, wherein X is O.

10. The compound of claim 1, wherein X is S.

11. The compound of claim 1, wherein n is 1 or 2.

12. The compound of claim 1, wherein n is 1.

13. The compound of claim 1, wherein n is 2.

14. The compound of claim 1, selected from:

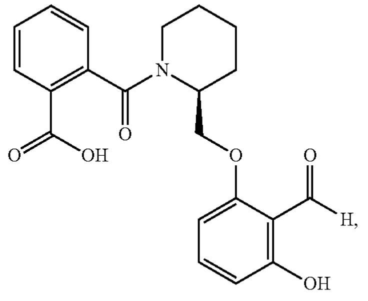

-continued
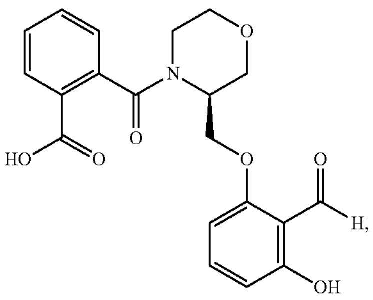
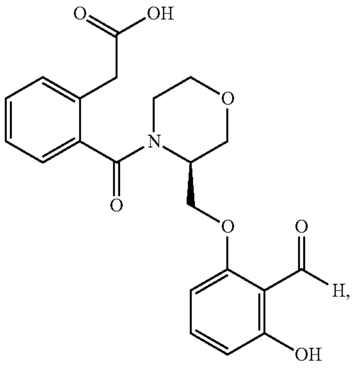
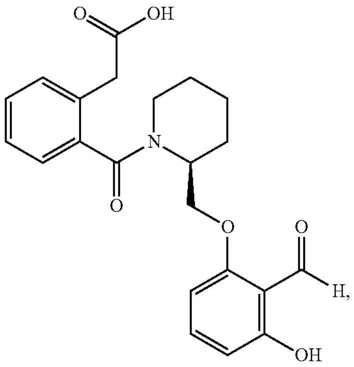
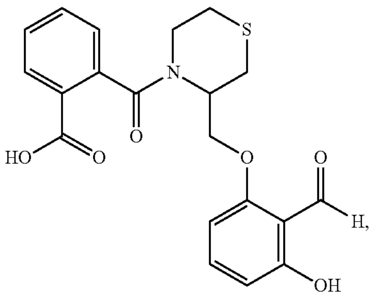
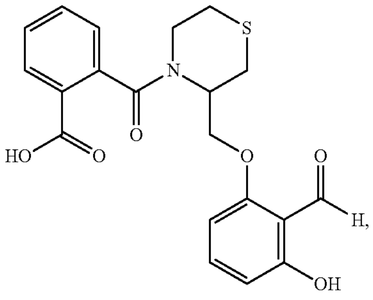
-continued
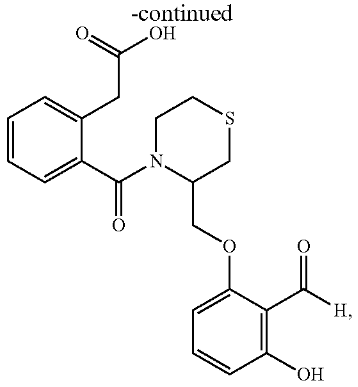
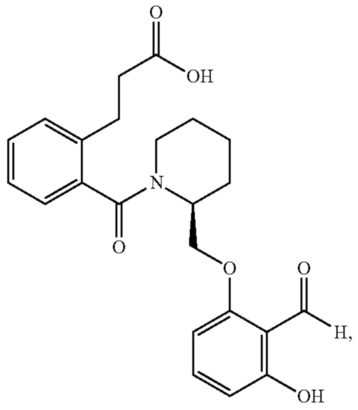
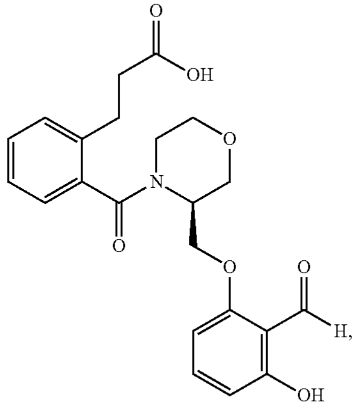
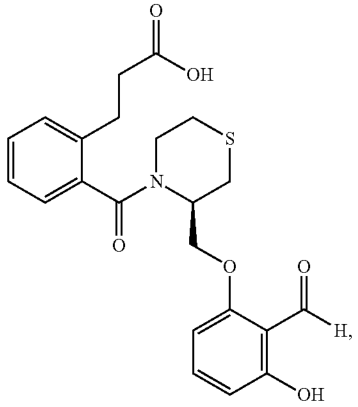

-continued
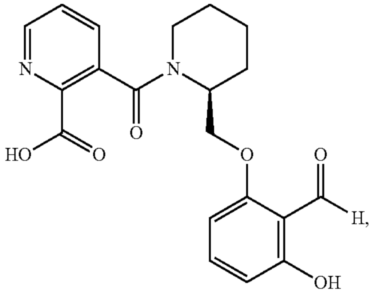
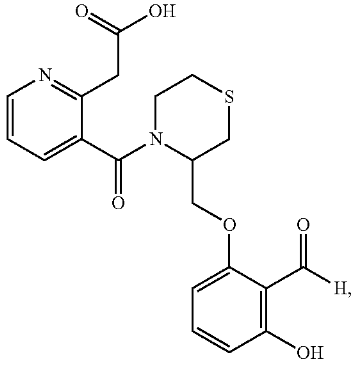
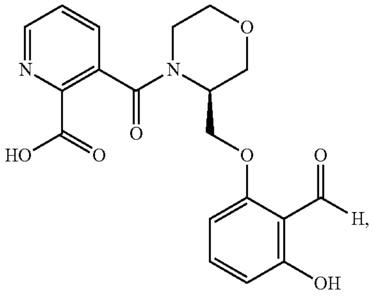
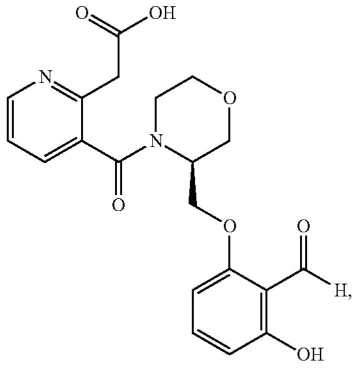
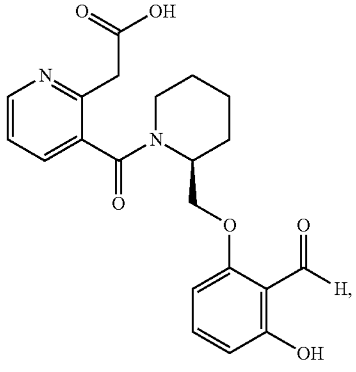
-continued
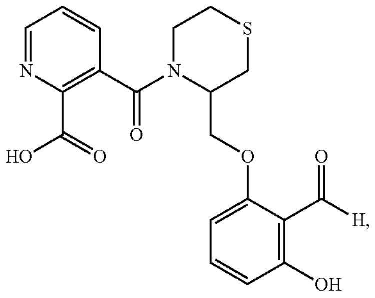
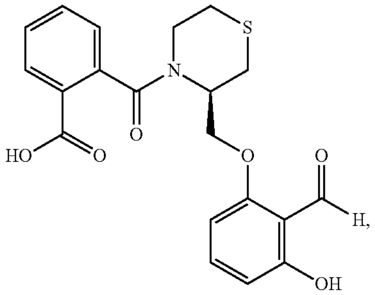
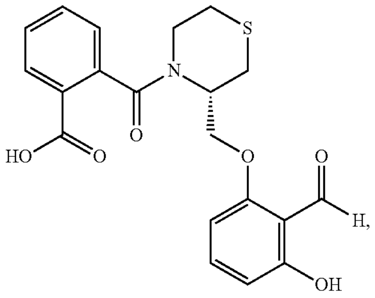
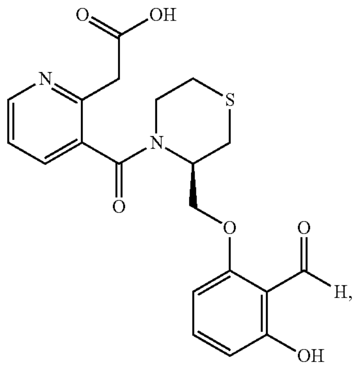
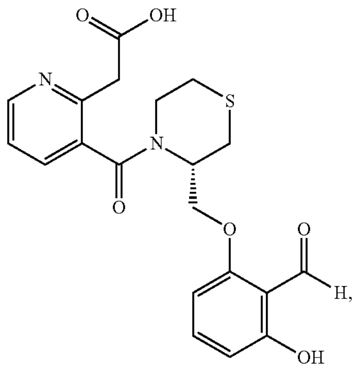

-continued

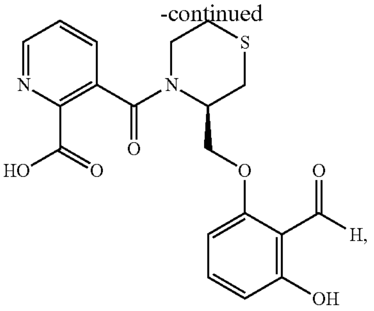

and

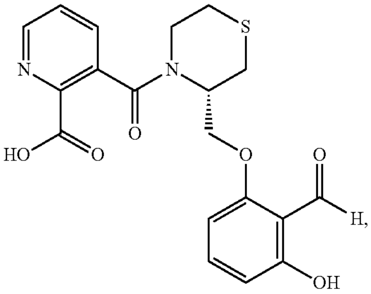

or an isotopically enriched analog, stereoisomer, mixture of stereoisomers, or prodrug thereof, or a pharmaceutically acceptable salt of each thereof.

15. A pharmaceutical composition comprising a compound according to claim 1, or an isotopically enriched analog, stereoisomer, mixture of stereoisomers, or prodrug thereof, or a pharmaceutically acceptable salt of each thereof, and a pharmaceutically acceptable excipient.

16. A method for increasing oxygen affinity of hemoglobin in a subject in need thereof, comprising administering to the subject a compound according to claim 1 or an isotopically enriched analog, stereoisomer, mixture of stereoisomers, or prodrug thereof, or a pharmaceutically acceptable salt of each thereof.

17. A method for treating a disorder mediated by hemoglobin in a subject in need thereof, comprising administering to the subject a compound according to claim 1, or an isotopically enriched analog, stereoisomer, mixture of stereoisomers, or prodrug thereof, or a pharmaceutically acceptable salt of each thereof.

18. The method of claim 16, wherein the hemoglobin is sickle hemoglobin.

19. A method for treating sickle cell disease in a subject in need thereof, comprising administering to the subject a compound according to claim 1, or an isotopically enriched analog, stereoisomer, mixture of stereoisomers, or prodrug thereof, or a pharmaceutically acceptable salt of each thereof.

20. A compound selected from:

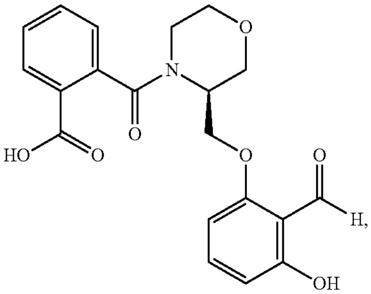

-continued

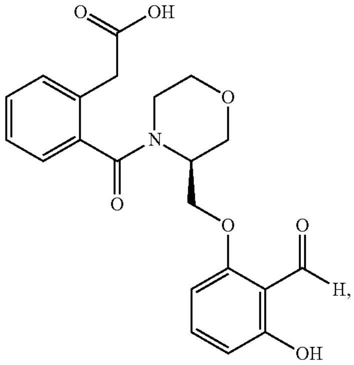

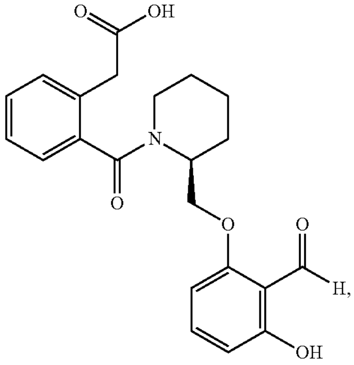

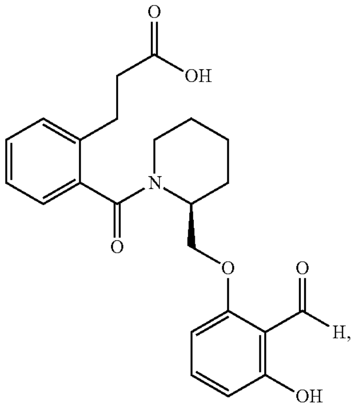

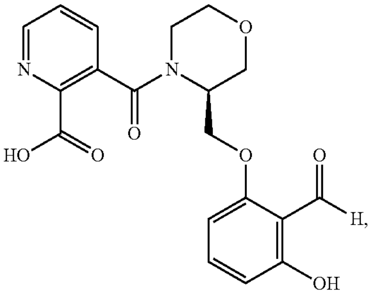

-continued
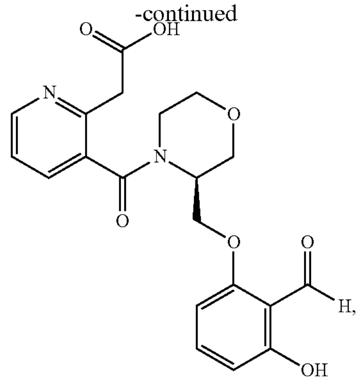
,
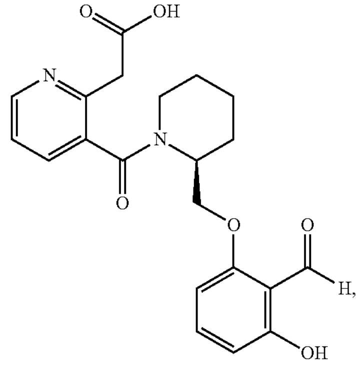
,
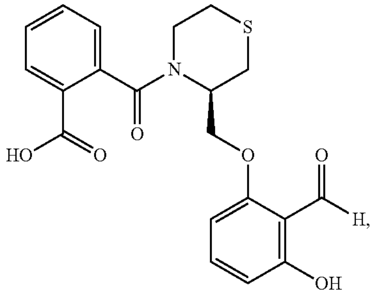
,
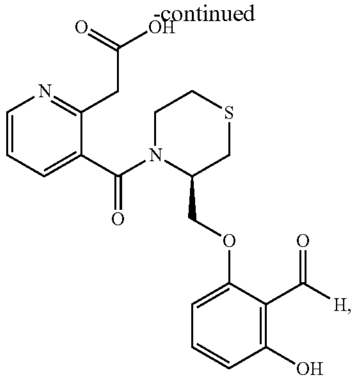
, and
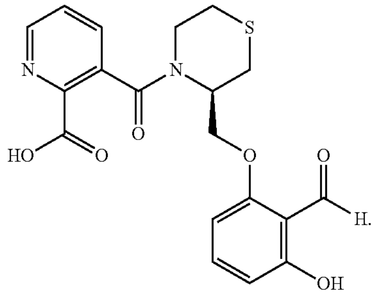
.
or an isotopically enriched analog, stereoisomer, mixture of stereoisomers, or prodrug thereof, or a pharmaceutically acceptable salt of each thereof.
* * * * *